US009850465B2

(12) United States Patent
Parent et al.

(10) Patent No.: US 9,850,465 B2
(45) Date of Patent: Dec. 26, 2017

(54) GENERATION OF THYMIC EPITHELIAL PROGENITOR CELLS IN VITRO

(71) Applicant: The Regents of the University of California, Oakland, CA (US)

(72) Inventors: Audrey Parent, San Francisco, CA (US); Matthias Hebrok, San Francisco, CA (US); Mark Stuart Anderson, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 5 days.

(21) Appl. No.: 14/770,625

(22) PCT Filed: Feb. 26, 2014

(86) PCT No.: PCT/US2014/018777
§ 371 (c)(1),
(2) Date: Aug. 26, 2015

(87) PCT Pub. No.: WO2014/134213
PCT Pub. Date: Sep. 4, 2014

(65) Prior Publication Data
US 2016/0010055 A1 Jan. 14, 2016

Related U.S. Application Data

(60) Provisional application No. 61/806,802, filed on Mar. 29, 2013, provisional application No. 61/770,266, filed on Feb. 27, 2013.

(51) Int. Cl.
*C12N 5/074* (2010.01)
*C12N 5/071* (2010.01)
*C12N 5/078* (2010.01)

(52) U.S. Cl.
CPC ........ *C12N 5/065* (2013.01); *C12N 2501/119* (2013.01); *C12N 2501/15* (2013.01); *C12N 2501/155* (2013.01); *C12N 2501/16* (2013.01); *C12N 2501/385* (2013.01); *C12N 2501/41* (2013.01); *C12N 2501/415* (2013.01); *C12N 2506/02* (2013.01); *C12N 2506/45* (2013.01)

(58) Field of Classification Search
CPC .......... C12N 5/00; C12N 5/06; C12N 5/0606; C12N 5/0607; C12N 5/0617; C12N 5/0688
See application file for complete search history.

(56) References Cited

U.S. PATENT DOCUMENTS

| | | | |
|---|---|---|---|
| 7,285,415 B2 | 10/2007 | Keirstead et al. | |
| 7,326,572 B2 | 2/2008 | Fisk et al. | |
| 7,510,876 B2 | 3/2009 | D'Amour et al. | |
| 8,216,836 B2 | 7/2012 | D'Amour et al. | |
| 8,247,229 B2 | 8/2012 | Odorico et al. | |
| 8,268,621 B2 | 9/2012 | Turovets et al. | |
| 9,234,170 B2 * | 1/2016 | Snoeck ............... | C12N 5/0617 |
| 2004/0096971 A1 | 5/2004 | Blackburn et al. | |
| 2006/0003446 A1 | 1/2006 | Keller et al. | |
| 2011/0287539 A1 | 11/2011 | Pauwelyn et al. | |
| 2012/0135519 A1 | 5/2012 | Ameri et al. | |
| 2012/0190112 A1 | 7/2012 | Davis et al. | |

FOREIGN PATENT DOCUMENTS

| | | |
|---|---|---|
| WO | WO2010091241 A2 | 8/2010 |
| WO | WO2010143529 A1 | 12/2010 |
| WO | WO2011139628 | 12/2010 |
| WO | WO2011064549 A2 | 6/2011 |
| WO | WO2011139628 | 11/2011 |
| WO | WO2011139628 A1 | 11/2011 |

OTHER PUBLICATIONS

Bayha, et al., "Retinoic Acid Signaling Organizes Endodermal Organ Specification along the Entire Antero-Posterior Axis", PLoS ONE. 2009; 4(6): e5845, pp. 1-15.
Anonymous: "JoVE / Peer Reviewed Scientific Video Journal—Generation of functional thymic epithelium from human embryonic stem cells that supports host T cell development," Feb. 26, 2013 (Feb. 26, 2013) URL:http://www.jove.com/visualize/abstract/23684540/generation-functional-thymic-epithelium-from-human-embryonic-stem.
Bayha, E., et al., "Retinoic Acid Signaling Organizes Endodermal Organ Specification along the Entire Antero-Posterior Axis," PLoS ONE (2009) 4(6):e5845. PDF file pp. 1-15. Abstract.
Gordon, J. and Manley, N., "Mechanisms of thymus organogenesis and morphogenesis," Development (2011) 138:3865-3878.
Inami, Y., et al., "Differentiation of induced pluripotent stem cells to thymic epithelial cells by phenotype," Immunology and Cell Biology (2011) 89:314-321.

(Continued)

*Primary Examiner* — Ruth Davis
(74) *Attorney, Agent, or Firm* — Shweta Chandra; Carol L. Francis; Bozicevic, Field & Francis LLP

(57) ABSTRACT

Methods for generating thymic epithelial progenitor (TEP) cells from pluripotent stem (PS) cells in vitro are provided. Compositions and systems of cell populations of TEP cells as well as cells formed during different stages of differentiation of PS cells into TEP cells are also disclosed. The methods, isolated in vitro cell populations, compositions, and systems disclosed provide functional TEP cells that mature into thymic epithelial cells in vivo.

19 Claims, 21 Drawing Sheets

(56) References Cited

OTHER PUBLICATIONS

Inman, G., et al., "SB-431542 Is a Potent and Specific Inhibitor of Transforming Growth Factor-β Superfamily Type I Activin Receptor-Like Kinase (ALK) Receptors ALK4, ALK5, and ALK7," Mol Pharmacol (2002) 62(1):65-74.

Lai, L.and Jin, J., "Generation of Thymic Epithelial Cell Progenitors by Mouse Embryonic Stem Cells," Stem Cells (2009) 27:3012-3020.

Mou, H., et al., "Generation of Multipotent Lung and Airway Progenitors from Mouse ESs and Patient-Specific Cystic Fibrosis iPSCs," Cell Stem Cell (2012) 10:385-397.

Parent, A.,et al., "Generation of Functional Thymic Epithelium from Human Embryonic Stem Cells that Supports Host T Cell Development,"Cell Stem Cell (2013) 13:219-229.

Yoshida, S., et al., "Generation of Stratified Squamous Epithelial Progenitor Cells from Mouse Induced Pluripotent Stem Cells," PLoS ONE (2011) 6(12):e28856 10 pp.

\* cited by examiner

FIG. 1
A
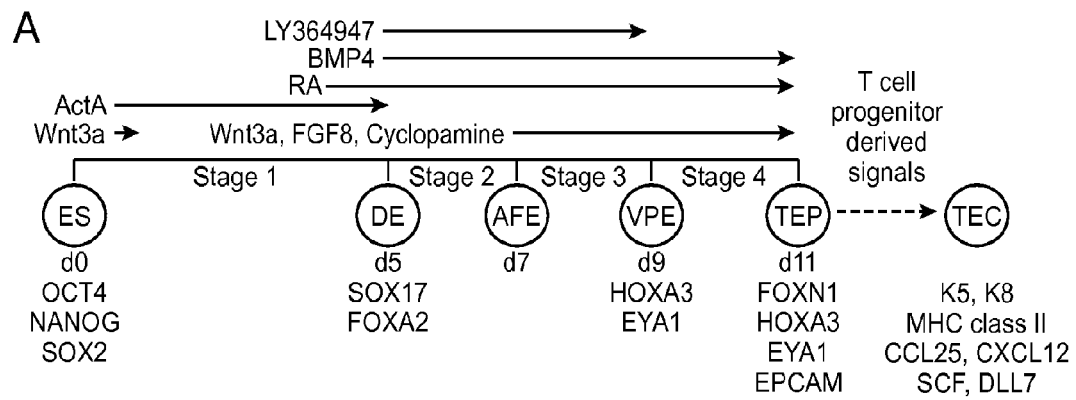
B
| Condition | Factors | | | |
|---|---|---|---|---|
| | Stage 1 | Stage 2 | Stage 3 | Stage 4 |
| 1 | None | None | None | None |
| 2 | Wnt3a d1+ ActA d1-5+ RA d4-5 | RA + LY | RA + LY | RA |
| 3 | Wnt3a d1+ ActA d1-5 | BMP4 + LY | BMP4 + LY | BMP4 |
| 4 | Wnt3a d1+ ActA d1-3+ RA d4-5 | RA + BMP4 + LY | RA + BMP4 + LY | RA + BMP4 |
| 5 | Wnt3a d1+ ActA d1-4+ RA d4-5 | RA + BMP4 + LY | RA + BMP4 + LY | RA + BMP4 |
| 6 | Wnt3a d1+ ActA d1-5+ RA d4-5 | RA + BMP4 + LY | RA + BMP4 + LY | RA + BMP4 |
| 7 | Wnt3a d1+ ActA d1-5+ RA d4-5 | RA + BMP4 + LY | RA + BMP4 + LY + Wnt3a +FGF8b + Cyc | RA + BMP4 + Wnt3a + FGF8b + Cyc |
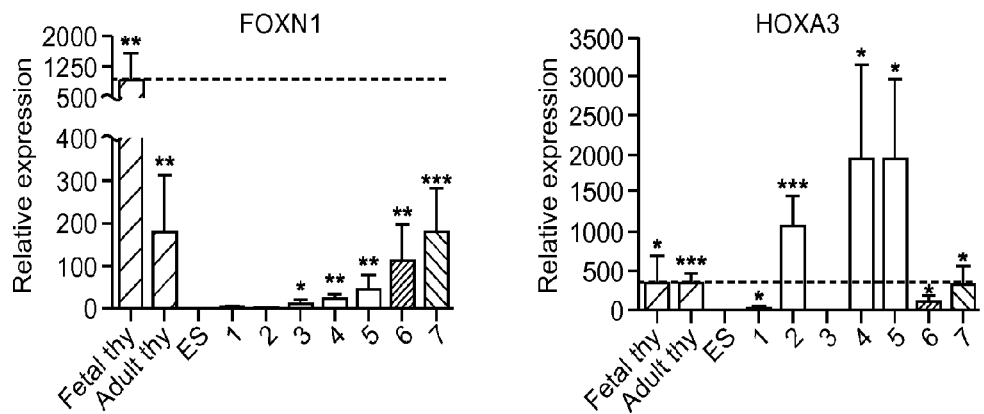
C
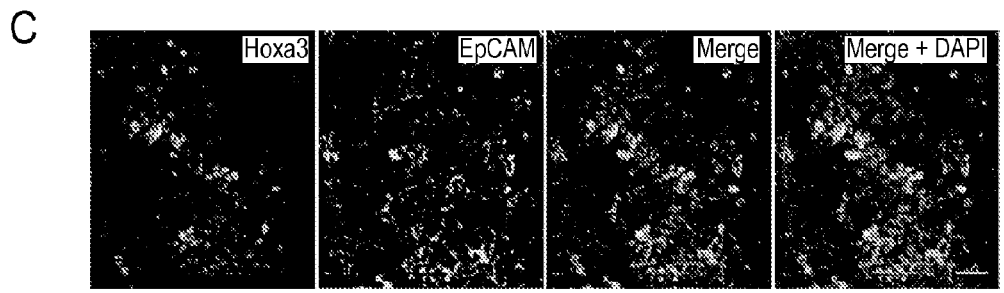

FIG. 2 (continued)
B
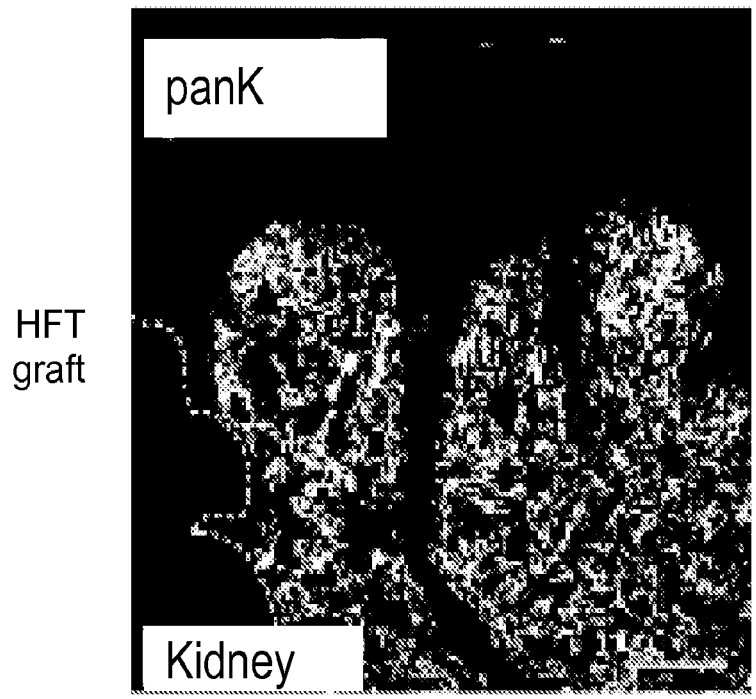

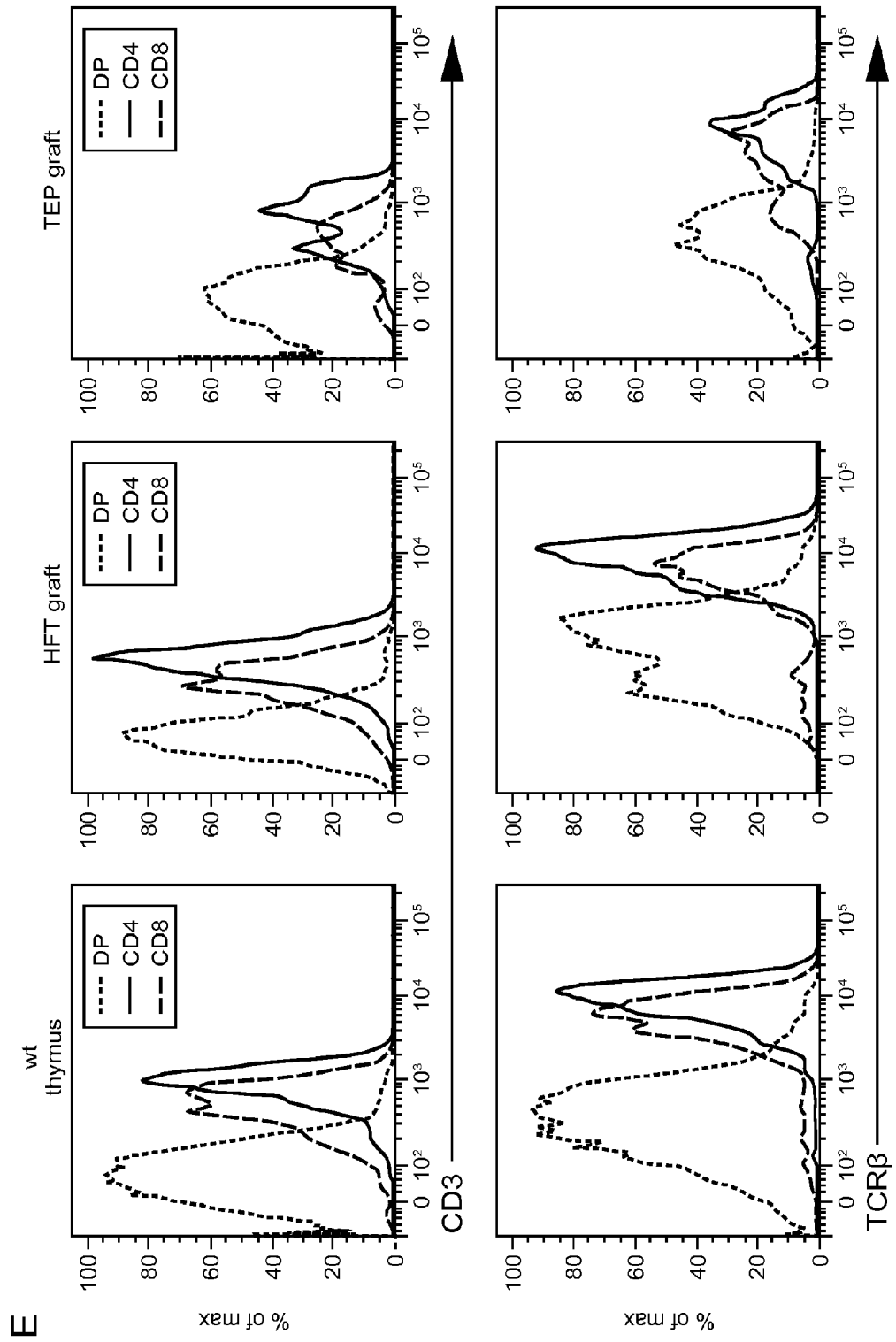

FIG. 5

| Day | 1 | 2 | 3 | 4 | 5 | 6 | 7 | 8 | 9 | 10 | 11 |
|---|---|---|---|---|---|---|---|---|---|---|---|
| Culture Condition | | Remove Wnt3a Add KSR | | Add RA Increase KSR | Remove KSR Add B27 | Remove ActA Add BMP4 Add LY364947 | | Decrease RA | | Remove LY364947 | |
| Medium | RPMI 1640 | RPMI 1640 | RPMI 1640 | RPMI 1640 | RPMI 1640 | RPMI 1640 | RPMI 1640 | DMEM/F12 | DMEM/F12 | DMEM/F12 | DMEM/F12 |
| Additives | Wnt3a 25 ng/ml ActA 100 ng/ml | ActA 100 ng/ml KSR 0.2% | ActA 100 ng/ml KSR 0.2% | ActA 100 ng/ml RA 0.25 μM KSR 2% | ActA 100 ng/ml RA 0.25 μM B27 0.5% | RA 0.25 μM BMP4 50 ng/ml LY364947 5 μM B27 0.5% | RA 0.25 μM BMP4 50 ng/ml LY364947 5 μM B27 0.5% | RA 0.1 μM BMP4 50 ng/ml LY364947 5 μM B27 0.5% | RA 0.1 μM BMP4 50 ng/ml LY364947 5 μM B27 0.5% | RA 0.1 μM BMP4 50 ng/ml B27 0.5% | RA 0.1 μM BMP4 50 ng/ml B27 0.5% |

FIG. 6

| Day | 1 | 2 | 3 | 4 | 5 | 6 | 7 | 8 | 9 | 10 | 11 |
|---|---|---|---|---|---|---|---|---|---|---|---|
| Culture Condition | | Remove Wnt3a Add KSR | | Add RA Increase KSR | Remove KSR Add B27 | Remove ActA Add BMP4 Add LY364947 | | Decrease RA Add Wnt3a Add FGF8b Add Cyclopamine | | Remove LY364947 | |
| Medium | RPMI 1640 | RPMI 1640 | RPMI 1640 | RPMI 1640 | RPMI 1640 | RPMI 1640 | RPMI 1640 | DMEM/F12 | DMEM/F12 | DMEM/F12 | DMEM/F12 |
| Additives | Wnt3a 25 ng/ml ActA 100 ng/ml | ActA 100 ng/ml KSR 0.2% | ActA 100 ng/ml KSR 0.2% | ActA 100 ng/ml RA 0.25 µM KSR 2% | ActA 100 ng/ml RA 0.25 µM B27 0.5% | RA 0.25 µM BMP4 50 ng/ml LY364947 5 µM B27 0.5% | RA 0.25 µM BMP4 50 ng/ml LY364947 5 µM B27 0.5% | Wnt3a 50 ng/ml RA 0.1 µM BMP4 50 ng/ml LY364947 5 µM FGF8b 50 ng/ml Cyclopamine 0.5 µM B27 0.5% | Wnt3a 50 ng/ml RA 0.1 µM BMP4 50 ng/ml LY364947 5 µM FGF8b 50 ng/ml B27 0.5% | Wnt3a 50 ng/ml RA 0.1 µM BMP4 50 ng/ml FGF8b 50 ng/ml B27 0.5% | Wnt3a 50 ng/ml RA 0.1 µM BMP4 50 ng/ml FGF8b 50 ng/ml B27 0.5% |

FIG. 7
A
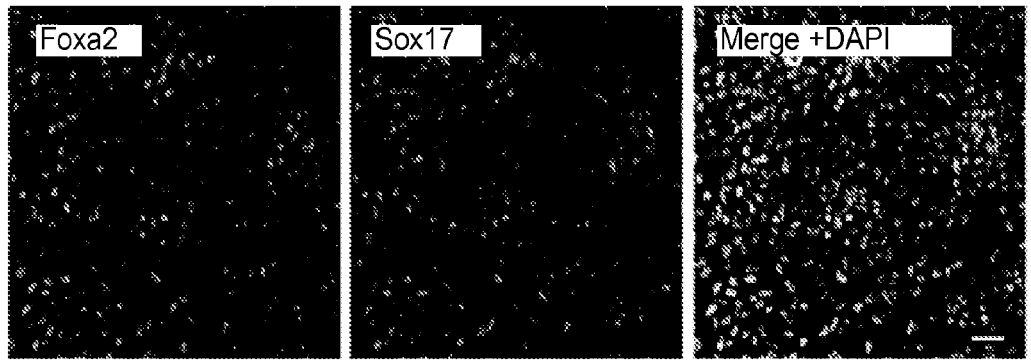
B
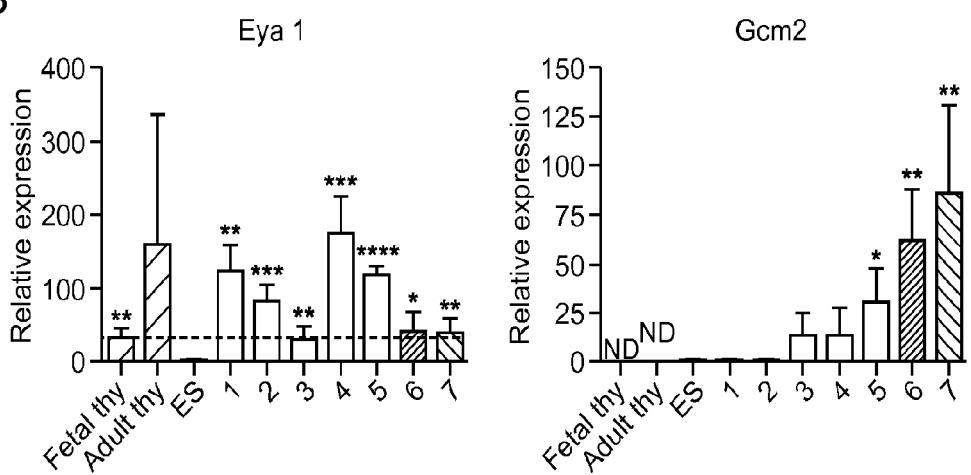
C
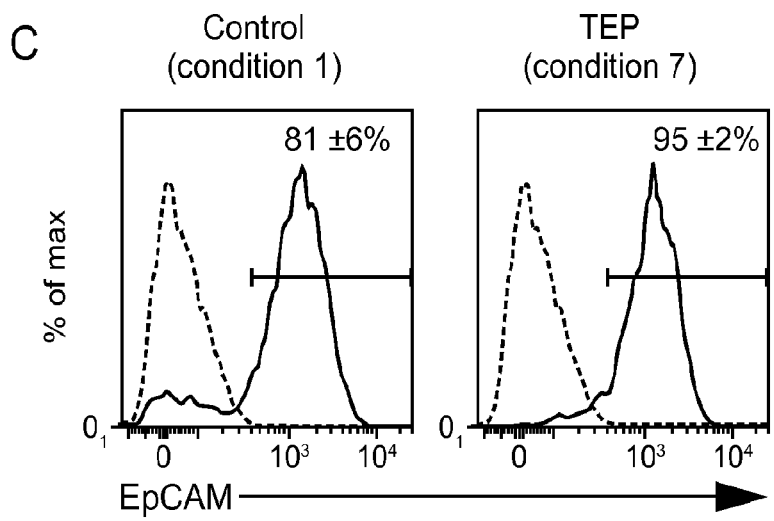

FIG. 7 (continued)
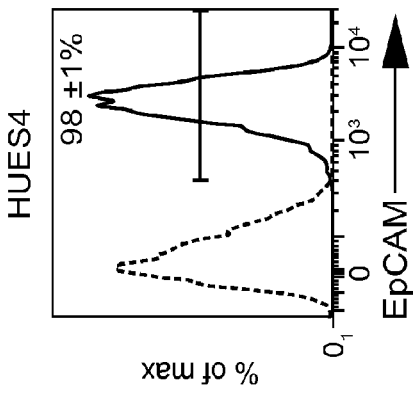
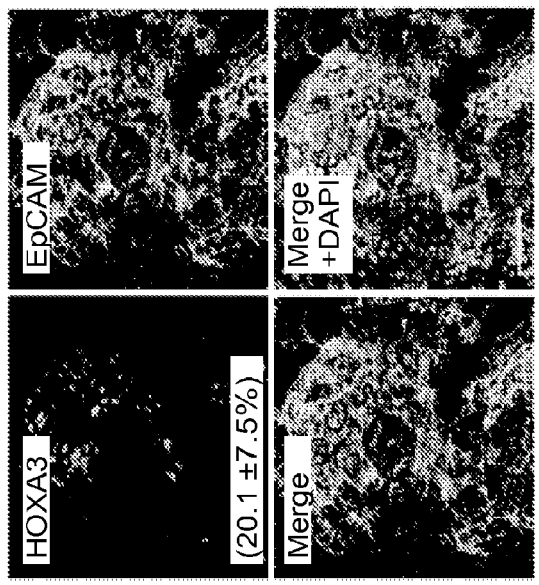
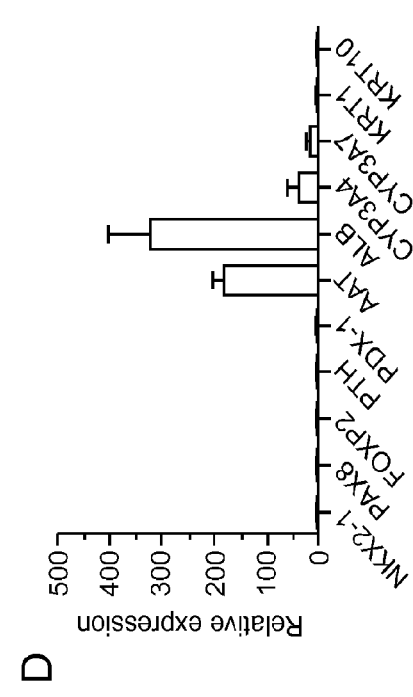
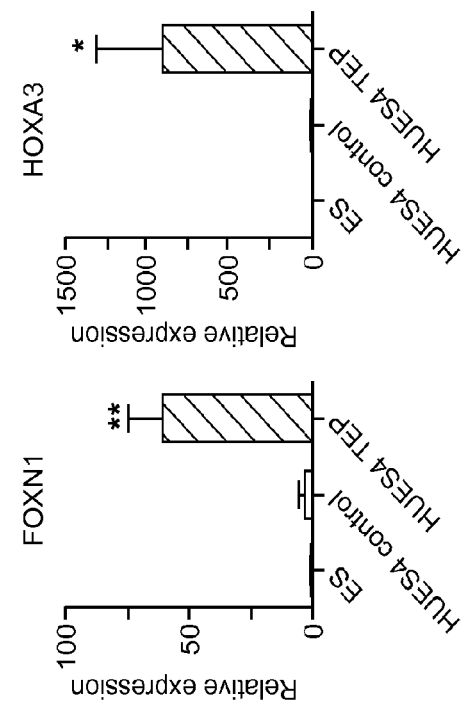

GENERATION OF THYMIC EPITHELIAL PROGENITOR CELLS IN VITRO

CROSS REFERENCE

This application claims the benefit of U.S. Provisional Patent Application No. 61/770,266 filed Feb. 27, 2013, and U.S. Provisional Patent Application No. 61/806,802 filed Mar. 29, 2013, which applications are incorporated herein by reference in their entirety.

INTRODUCTION

The use of stem cells to replace lost or damaged tissue represents one of the most promising applications of stem cell research.

Among the most interesting and clinically relevant cell types that are yet to be successfully generated from human pluripotent stem cells are thymic epithelial progenitor cells.

Thymic epithelial progenitor (TEP) cells give rise to two populations of mature thymic epithelial cells in the thymus: cortical thymic epithelial cells and medullary thymic epithelial cells. The thymus plays a crucial role in the immune system by supporting the development of functional T cells. It is also the main organ involved in establishing immune tolerance through the elimination of autoreactive T cell subsets and through the production of regulatory T cells (reviewed in (Anderson et al., Nat Rev Immunol 7, 954-963, 2007). Both of these critical functions are mediated by thymic epithelial cells, the main component of the thymic stroma.

As such, there is a need for methods for generating functional TEP cells and for cell populations enriched in functional TEP cells that can differentiate into functional thymic epithelial cells.

SUMMARY OF THE INVENTION

Methods and compositions for generating thymic epithelial progenitor (TEP) cells are provided. In general the method involves in vitro generation of TEP cells from pluripotent stem cells. Compositions and systems of cell populations of TEP cells as well as cells formed during different stages of differentiation of PS cells into TEP cells are also disclosed. The TEP cells generated by the methods disclosed herein are functional and generate functional thymic epithelial cells when transplanted in vivo.

In certain embodiments, the method for generating thymic epithelial progenitor (TEP) cells includes culturing definitive endodermal (DE) cells obtained from pluripotent stem cells in a medium comprising an activator of retinoic acid receptor, an activator of bone morphogenetic protein (BMP) signaling, and an inhibitor of transforming growth factor-β (TGF-β) signaling. In certain embodiments, the DE cells are obtained from pluripotent stem cells by culturing the pluripotent stem cells in a medium that includes a growth factor which may be Nodal, Activin A, and/or Activin B.

In certain embodiments, the method includes culturing anterior foregut endodermal (AFE) cells produced by the culturing of the DE cells, wherein the culturing of the AFE cells is in a medium that includes an activator of retinoic acid receptor, an activator of BMP signaling, and an inhibitor of TGF-β signaling.

In certain embodiments, the method includes culturing anterior foregut endodermal (AFE) cells produced by the culturing of the DE cells, wherein the culturing of the AFE cells is in a medium that includes an activator of retinoic acid receptor, an activator of BMP signaling, an inhibitor of TGF-β signaling, a Wnt family member, a FGF, and an inhibitor of Hedgehog signaling.

In certain embodiments, the method includes culturing ventral pharyngeal endodermal (VPE) cells produced by the culturing of the AFE cells, wherein the culturing of the VPE cells is in a medium comprising an activator of retinoic acid receptor and an activator of BMP signaling.

In certain embodiments, the method includes culturing ventral pharyngeal endodermal (VPE) cells produced by the culturing of the AFE cells, wherein the culturing of the VPE cells is in a medium comprising an activator of retinoic acid receptor, an activator of BMP signaling, a Wnt family member, a FGF, and an inhibitor of Hedgehog signaling.

In certain embodiments, a method for generating thymic epithelial progenitor (TEP) cells is provided. The method includes culturing AFE cells obtained from pluripotent stem cells in a medium comprising an activator of retinoic acid receptor, an activator of BMP signaling, and an inhibitor of TGF-β signaling.

In certain embodiments, the method may include culturing AFE cells obtained from pluripotent stem cells in a medium comprising an activator of retinoic acid receptor, an activator of BMP signaling, an inhibitor of TGF-β signaling, a Wnt family member, a FGF, and an inhibitor of Hedgehog signaling.

In certain embodiments, the method includes culturing ventral pharyngeal endodermal (VPE) cells produced by said culturing of the AFE cells, wherein the culturing of the VPE cells is in a medium comprising an activator of retinoic acid receptor and an activator of BMP signaling.

In certain embodiments, the method includes culturing ventral pharyngeal endodermal (VPE) cells produced by said culturing of the AFE cells, wherein the culturing of the VPE cells is in a medium comprising an activator of retinoic acid receptor, an activator of BMP signaling, a Wnt family member, a FGF, and an inhibitor of Hedgehog signaling.

In certain embodiments, a method for generating thymic epithelial progenitor (TEP) cells is provided. The method includes culturing ventral pharyngeal endodermal (VPE) cells obtained from pluripotent stem cells in a medium comprising an activator of retinoic acid receptor and an activator of BMP signaling.

In certain embodiments, the method includes culturing ventral pharyngeal endodermal (VPE) cells obtained from pluripotent stem cells in a medium comprising an activator of retinoic acid receptor, an activator of BMP signaling, a Wnt family member, a FGF, and an inhibitor of Hedgehog signaling.

In certain embodiments, the pluripotent stem cells used in the methods described herein may be embryonic stem cell, embryonic germ cells, or induced pluripotent stem cell. In certain embodiments, the pluripotent stem cells may be primate pluripotent stem cells (pPS) cells. In certain embodiments, the pPS cells may be human pluripotent stem (hPS) cells. In certain embodiments, the hPS cells may be human embryonic stem (hES) cells. In certain embodiments, the hPS cells may be induced pluripotent stem (iPS) cells.

Also disclosed herein are in vitro compositions that include isolated thymic epithelial progenitor (TEP) cells, an activator of retinoic acid receptor; and an activator of BMP signaling. In certain embodiments, the composition may further include a Wnt family member; a fibroblast growth factor; and an inhibitor of hedgehog signaling.

Also disclosed herein are compositions that include isolated definitive endodermal (DE) cells; an activator of retinoic acid receptor; an activator of BMP signaling; and an inhibitor of TGF-β signaling.

Also disclosed herein are compositions that include isolated anterior foregut endodermal (AFE) cells; an activator of retinoic acid receptor; an activator of BMP signaling; and an inhibitor of TGF-β signaling. In certain embodiments, the composition that includes isolated AFE cells may further include a Wnt family member; a fibroblast growth factor; and an inhibitor of hedgehog signaling.

Also disclosed herein are compositions that include isolated ventral pharyngeal endodermal (VPE) cells; an activator of retinoic acid receptor; an activator of BMP signaling; and an inhibitor of TGF-β signaling. In certain embodiments, the composition that includes isolated VPE cells may further include a Wnt family member; a fibroblast growth factor; and an inhibitor of hedgehog signaling.

Also disclosed herein are compositions that include isolated VPE cells; an activator of retinoic acid receptor; and an activator of BMP signaling. In certain embodiments, the composition may further include a Wnt family member; a fibroblast growth factor; and an inhibitor of hedgehog signaling.

Provided herein is a first in vitro cell population including primate cells and a second in vitro cell population comprising progeny of a portion of the first in vitro cell population, wherein the progeny are TEP cells. The TEP cells may express FOXN1. The first in vitro cell population may be primate pluripotent stem cells, DE cells, AFE cells, or VPE cells.

Also described are a first in vitro cell population including primate pluripotent stem cells and a second in vitro cell population comprising progeny of a portion of the first in vitro cell population, wherein the progeny are DE cells, AFE cells, or VPE cells.

A system for generating TEP cells is disclosed. The system may include a line of undifferentiated human PS cells; and a cell population of TEP cells differentiated therefrom, where the TEP cells express one or more of the TEP cell markers.

In certain embodiments, the system may include a cell population of human DE cells, and a cell population of TEP cells differentiated therefrom. Also, the system may include a cell population of human AFE cells; and a cell population of TEP cells differentiated therefrom. The system may include a cell population of human VPE cells; and a cell population of TEP cells differentiated therefrom.

In another example, the system for generating TEP cells may include a cell population of human PS cells and a cell population of DE cells differentiated therefrom. The system may include a cell population of human PS cells; and a cell population of AFE cells differentiated therefrom. The system may include a cell population of human PS cells and a cell population of VPE cells differentiated therefrom, wherein the VPE cells express one or more of the VPE cell markers. The system may include a cell population of human PS cells, a cell population of DE cells differentiated from the PS cells, a cell population of AFE cells differentiated from the DE cells, a cell population of VPE cells differentiated from the AFE cells, and a cell population of TEP cells differentiated from the AFE cells.

BRIEF DESCRIPTION OF THE DRAWINGS

FIG. 1 (A-C) illustrates directed differentiation of hESCs into TEP cells in vitro.

FIG. 5 provides an exemplary protocol for generation of TEP cells from ES cells.

FIG. 6 provides an exemplary protocol for generation of TEP cells from ES cells.

FIG. 7 (A-G) illustrates induction of DE, PE, and TEP markers in hESC cultures.

DEFINITIONS

Figure 2:
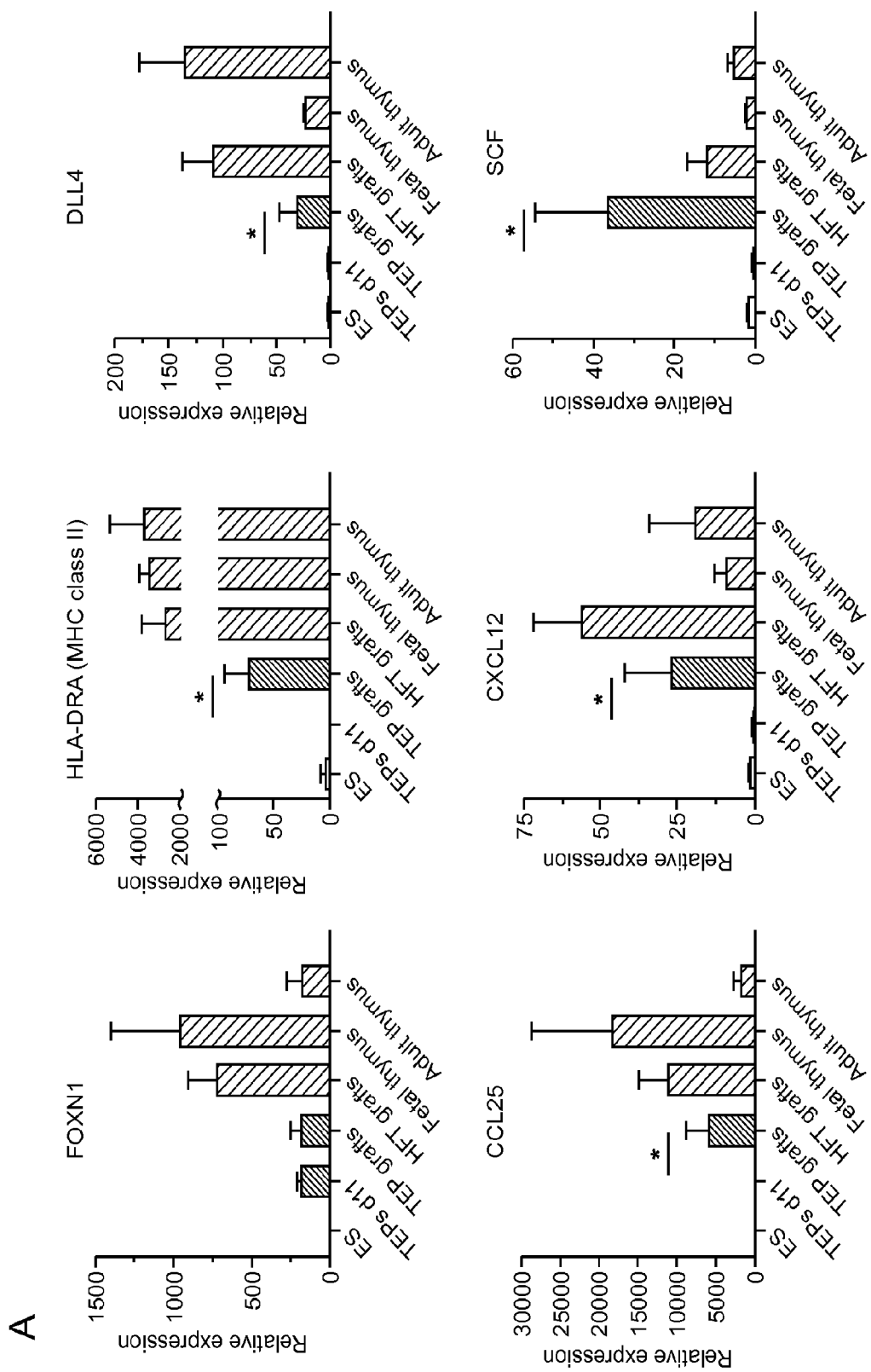
FIG. 2 (A-C) illustrates maturation of hESC derived TEP cells into TECs in vivo.
Figure 2:
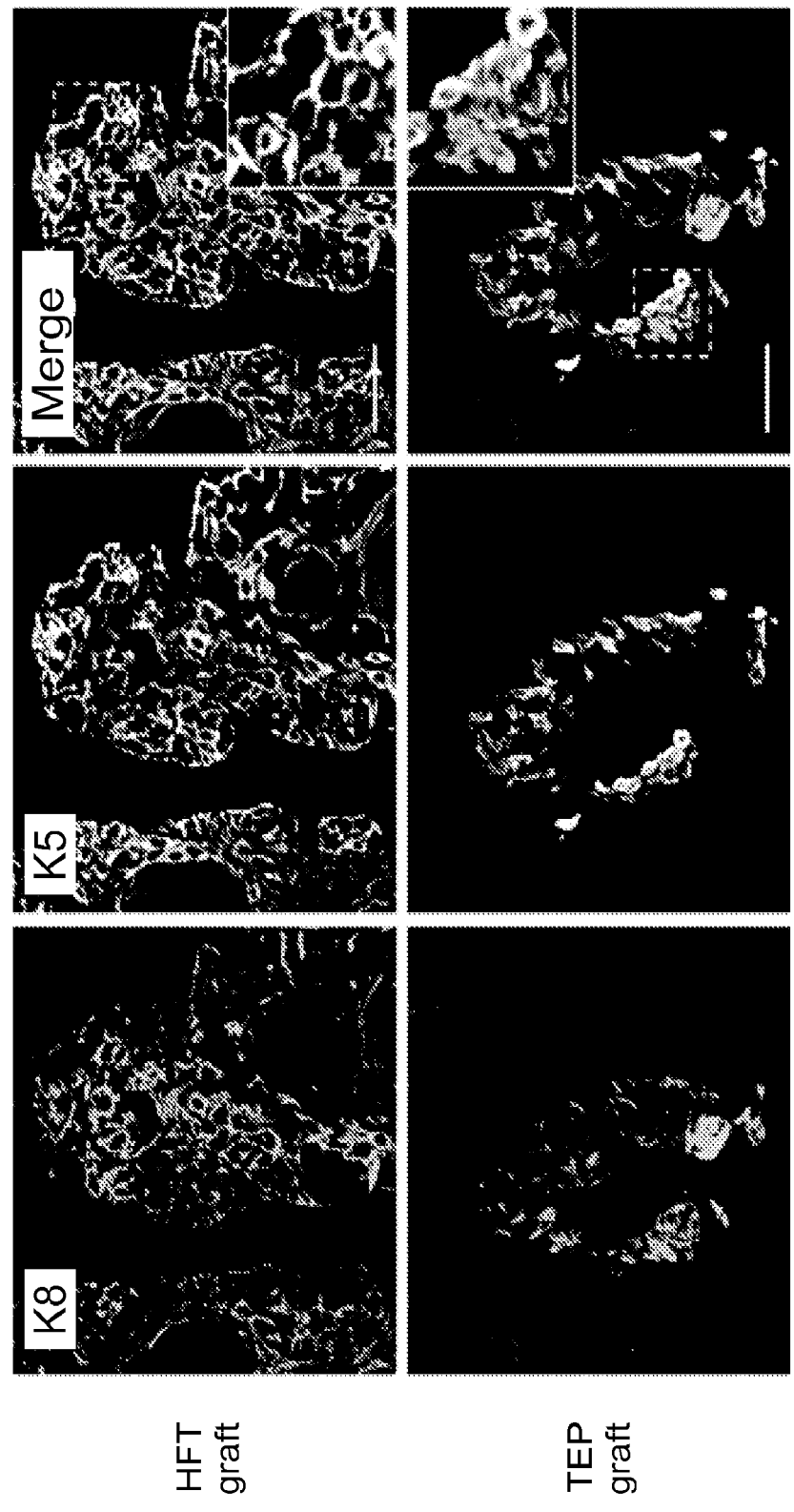

By "pluripotent stem cell" or "pluripotent cell" it is meant a cell that has the ability under appropriate conditions of producing progeny of several different cell types that are derivatives of all of the three germinal layers (endoderm, mesoderm, and ectoderm) Pluripotent stem cells are capable of forming teratomas. Examples of pluripotent stem cells are embryonic stem (ES) cells, embryonic germ stem (EG) cells, induced pluripotent stem (iPS) cells, and adult stem cells. PS cells may be from any organism of interest, including, primate, e.g., human; canine; feline; murine; equine; porcine; avian; camel; bovine; ovine, and so on.

By "embryonic stem cell" or "ES cell" it is meant a cell that a) can self-renew, b) can differentiate to produce all types of cells in an organism, and c) is derived from a developing organism or is an established ES cell line which was derived from a developing organism. ES cell may be derived from the inner cell mass of the blastula of a developing organism. ES cell may be derived from a blastomere generated by single blastomere biopsy (SBB) involving removal of a single blastomere from the eight cell stage of a developing organism. In general, SBB provides a non-destructive alternative to inner cell mass isolation. SBB and generation of hES cells from the biopsied blastomere is described in Cell Stem Cell, 2008 Feb. 7; 2(2):113-7. ES cells can be cultured over a long period of time while maintaining the ability to differentiate into all types of cells in an organism. In culture, ES cells typically grow as flat colonies with large nucleo-cytoplasmic ratios, defined borders and prominent nuclei. In addition, ES cells express SSEA-3, SSEA-4, TRA-1-60, TRA-1-81, and Alkaline Phosphatase, but not SSEA-1. Examples of methods of generating and characterizing ES cells may be found in, for example, U.S. Pat. No. 7,029,913, U.S. Pat. No. 5,843,780, and U.S. Pat. No. 6,200,806, the disclosures of which are incorporated herein by reference.

By "embryonic germ stem cell", embryonic germ cell" or "EG cell" it is meant a cell that a) can self-renew, b) can differentiate to produce all types of cells in an organism, and c) is derived from germ cells and germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPS cell" it is meant a cell that a) can self-renew, b) can differentiate to produce all types of cells in an organism, and c) is derived from a somatic cell. iPS cells have an ES cell-like morphology, growing as flat colonies with large nucleo-cytoplasmic ratios, defined borders and prominent nuclei. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. iPS cells may be generated by providing the cell with "reprogramming factors", i.e., one or more, e.g., a cocktail, of biologically active factors that act on a cell to alter transcription, thereby reprogramming a cell to pluripotency. Examples of methods of generating and characterizing iPS cells may be found in, for example, Application Nos. US20090047263, US20090068742, US20090191159, US20090227032, US20090246875, and US20090304646, the disclosures of which are incorporated herein by reference.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e., ectoderm, mesoderm and endoderm. For example, somatic cells would include both neurons and neural progenitors, the latter of which may be able to self-renew and naturally give rise to all or some cell types of the central nervous system but cannot give rise to cells of the mesoderm or endoderm lineages.

The term "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time).

By "endoderm" it is meant the germ layer formed during animal embryogenesis that gives rise to the gastrointestinal tract, respiratory tract, endocrine glands and organs, certain structures of the auditory system, and certain structures of the urinary system.

By "mesoderm" it is meant the germ layer formed during animal embryogenesis that gives rise to muscles, cartilage, bones, dermis, the reproductive system, adipose tissue, connective tissues of the gut, peritoneum, certain structures of the urinary system, mesothelium, notochord, and spleen.

By "ectoderm" it is meant the germ layer formed during animal embryogenesis that gives rise to the nervous system, tooth enamel, epidermis, hair, nails, and linings of mucosal tissues.

By "bone morphogenic proteins" or "BMPs" it is meant the family of growth factors that is a subfamily of the transforming growth factor β (TGF β) superfamily. BMPs (e.g. BMP1, BMP2, BMP3, BMP4, BMP5, BMP6, BMP7, BMP8a, BMP8b, BMP9/GDF, BMP10, BMP11/GDF11, BMP12/GDF7, BMP13/GDF6, BMP14/GDF5, BMP15/GDF9B) were first discovered by their ability to induce the formation of bone and cartilage. BMPs interact with specific receptors on the cell surface, referred to as bone morphogenetic protein receptors (BMPRs). Signal transduction through BMPRs results in mobilization of members of the SMAD family of proteins, which in turn modulate transcription of target genes. Of particular interest in the present invention are activators of BMP signaling, which can readily be identified by one of ordinary skill in the art by any of a number of methods, for example competitive binding assays for binding to BMP or BMP receptors, functional assays, e.g., measuring enhancement of activity of downstream signaling proteins such as relocalization of SMADs, such as, BR-Smad to the nucleus and transcriptional activation of downstream gene targets as known in the art.

By "transforming growth factor betas", "TGF-βs", and "TGFBs" it is meant the TGFB secreted proteins belonging to the subfamily of the transforming growth factor β (TGFβ) superfamily. TGFBs (TGFB1, TGFB2, TGFB3) are multifunctional peptides that regulate proliferation, differentiation, adhesion, and migration and in many cell types. The mature peptides may be found as homodimers or as heterodimers with other TGFB family members. TGFBs interact with transforming growth factor beta receptors (TGF-βRs, or TGFBRs) on the cell surface, which binding activates MAP kinase-, Akt-, Rho- and Rac/cdc42-directed signal transduction pathways, the reorganization of the cellular architecture and nuclear localization of SMAD proteins, and the modulation of target gene transcription. Of particular interest in the present invention are inhibitors of TGFB signaling, which can be readily be identified by one of ordinary skill in the art by any of a number of methods, for example competitive binding assays for binding to TGFB or TGFB receptors, or functional assays, e.g. measuring suppression of activity of downstream signaling proteins such as MAPK, Akt, Rho, Rac, and SMADs, e.g., AR-Smad, etc., as well known in the art.

By "Wnts" it is meant the family of highly conserved secreted signaling molecules which play key roles in both embryogenesis and mature tissues. The human Wnt gene family has at least 19 members (Wnt-1, Wnt-2, Wnt-2B/Wnt-13, Wnt-3, Wnt3a, Wnt-4, Wnt-5A, Wnt-5B, Wnt-6, Wnt-7A, Wnt-7B, Wnt-8A, Wnt-8B, Wnt-9A/Wnt-14, Wnt-9B/Wnt-15, Wnt-10A, Wnt-10B, Wnt-11, Wnt-16). Wnt proteins modulate cell activity by binding to Wnt receptor complexes that include a polypeptide from the Frizzled (Fz) family of proteins and a polypeptide of the low-density lipoprotein receptor (LDLR)-related protein (LRP) family of proteins. Once activated by Wnt binding, the Wnt receptor complex will activate one or more intracellular signaling cascades. These include the canonical Wnt signaling pathway; the Wnt/planar cell polarity (Wnt/PCP) pathway; and the Wnt-calcium (Wnt/Ca2+) pathway.

By culturing under "non-adherent conditions" it is meant culturing under conditions that suppress the adhesion of cells to the vessel in which they are cultured, e.g. the bottom of a tissue culture plate or flask. In some instances, the cells are naturally non-adherent, i.e., they will not adhere to a surface unless the surface is coated with a matrix composition, e.g. fibronectin, laminin, poly-ornithin, poly-lysine, collagen IV, matrigel, and polycarbonate membranes. In some instances, cells may be maintained in a non-adherent state by agitating the culture.

By culturing under "adherent conditions" it is meant culturing under conditions that promote the adhesion of cells to the container in which they are cultured, e.g. the bottom of a tissue culture plate or flask. In some instances, cells may be induced to adhere to the container simply by keeping the culture stationary. In some instances, the wall of the container to which it is desirable to promote adhesion may be coated with a composition to which the cells may adhere, e.g. fibronectin, laminin, poly-ornithin, poly-lysine, collagen IV, matrigel, and polycarbonate membranes.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual", "subject", "host", and "patient" are used interchangeably herein and refer to any mammalian subject for whom diagnosis, treatment, or therapy is desired, particularly humans.

The term "medium" in context of cell culture or the phrase "cell culture medium" or "cell medium" refer to a cellular growth medium suitable for culturing of PS cells, DE cells, AFE cells, VPE cells, TEP cells. Examples of cell culture medium include Minimum Essential Medium (MEM), Eagle's Medium, Dulbecco's Modified Eagle Medium (DMEM), Dulbecco's Modified Eagle Medium: Nutrient Mixture F-12 (DMEM/F12), F10 Nutrient Mixture, Ham's F10 Nutrient Mix, Ham's F12 Nutrient Mixture, Medium 199, RPMI, RPMI 1640, reduced serum medium, basal medium (BME), DMEM/F12 (1:1), and the like, and combinations thereof. The medium or cell culture medium may be modified by adding one or more additives. Additives may include serum, such as, fetal bovine serum and/or serum replacement agents, such as, B27, N2, KSR, and combinations thereof, and differentiation factors, such as, activators of RA receptor, nodal, Act-A, Act-B, Wnt family members, activators of BMP signaling, inhibitors of TGF-β signaling, FGF, inhibitors of hedgehog signaling, and the like, and combinations thereof.

The term "isolated" in context of cells or cell population refers to cells that are in an environment other than their native environment, such as, apart from tissue of an organism.

The phrase "differentiation factors" as used herein refers to the agents that are included in the medium for culturing cells of the present disclosure, which agents promote the differentiation of the cells from a first cell type to a second cell type.

As used herein, "expression" and grammatical equivalents thereof, in the context of a marker, refers to production of the marker as well as level or amount of the marker. For example, expression of a marker or presence of a marker in a cell or a cell is positive for a marker, refers to expression of the marker at a level that is similar to a positive control level. The positive control level may be determined by the level of the marker expressed by a cell known to have the cell fate associated with the marker. Similarly, absence of expression of a marker or a cell is negative for a marker, refers to expression of the marker at a level that is similar to a negative control level. The negative control level may be determined by the level of the marker expressed by a cell known to not have the cell fate associated with the marker. As such, absence of a marker does not simply imply an undetectable level of expression of the marker, in certain cases, a cell may express the marker but the expression may be low compared to a positive control or may be at a level similar to that of a negative control.

As used herein, "marker" refers to any molecule that can be measured or detected. For example, a marker can include, without limitations, a nucleic acid, such as, a transcript of a gene, a polypeptide product of a gene, a glycoprotein, a carbohydrate, a glycolipid, a lipid, a lipoprotein, a carbohydrate, or a small molecule (for example, a molecule having a molecular weight of less than 10,000 amu).

A "variant" polypeptide means a biologically active polypeptide as defined below having at least 70%, 75%, 80%, 85%, 90%, 95%, 98%, or 99% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, at least about 95%, or at least about 99%. The variant polypeptides can be naturally or non-naturally glycosylated, i.e., the polypeptide has a glycosylation pattern that differs from the glycosylation pattern found in the corresponding naturally occurring protein. The variant polypeptides can have post-translational modifications not found on the natural polypeptide.

As used here in "analog" or "functional analog" in the context of a molecule, such as a ligand, a peptide, a polypeptide, or the like, refers to a molecule having similar functional properties but a different structure compared to the naturally occurring form of that molecule. In certain cases, the functional analog may be a small molecule that, for example, exhibits the function of a polypeptide. Any functional analog of the differentiation factors disclosed herein may be used in the methods and may be present in the compositions described herein. Such functional analogs are described in the literature and can also be identified by screening of library of compounds, such as, combinatorial compound libraries, peptide libraries, and the like.

The terms 'enriching" or "enriched" are used interchangeably herein and mean that the yield (fraction) of cells of one type is increased by at least 10% over the fraction of cells of that type in the starting culture or preparation.

DETAILED DESCRIPTION

Methods and compositions for generating thymic epithelial progenitor (TEP) cells are provided. In general the method involves in vitro generation of TEP cells from pluripotent stem cells. The TEP cells generated by the methods disclosed herein are functional and generate thymic epithelial cells in vivo.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the culture condition" includes reference to one or more culture conditions and equivalents thereof, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Generating Thymic Epithelial Cells In Vitro

A general overview of production of TEP cells from PS cells is provided in FIG. 1, Panel A. Production of TEP cells from PS cells involve four stages of differentiation:

Stage 1: Culturing of PS cells under conditions suitable to produce DE cells

Stage 2: Culturing of DE cells under conditions suitable to produce AFE cells

Stage 3: Culturing of AFE cells under conditions suitable to produce VPE cells

Stage 4: Culturing of VPE cells under conditions suitable to produce TEP cells

Culturing at each stage is conducted under culture conditions and for a time sufficient to produce the product of that stage, where the product may be characterized by expression of one or more markers and/or by functional characterization as described in more detail below. The culture medium of each of these stages is described below in more detail below.

The methods of the present disclosure contemplate methods that begin at any stage as set out above.

Stage 1: Culturing of pPS Cells to Produce DE Cells

As noted above, a method for generating thymic epithelial progenitor (TEP) cells from PS cells in vitro is provided.

In certain embodiments, the method includes differentiation of PS cells into DE cells. PS cells may be differentiated into DE cells by culturing the pluripotent stem cells in a medium comprising a growth factor, which can be one or more of Nodal, Activin A, and Activin B, or variants or analogs thereof. In certain cases, the medium for culturing the PS cells for inducing differentiation into DE cells may include a combination of Activin A and Activin B.

In certain cases, the medium for culturing the PS cells for inducing differentiation into DE cells may include one or more of Nodal, Activin A, Activin B in combination with an activator of BMP signaling. In certain cases, the medium for inducing differentiation of PS cells in to DE cells may include one or both of Activin A and Activin B in combination with an activator of BMP signaling.

In certain cases, the medium for inducing differentiation of PS cells into DE cells may include one or more of Nodal, Activin A, Activin B, an activator of BMP signaling, and a Wnt family member.

PS cells may be cultured in a differentiation medium that includes one or more of Nodal, Activin A, Activin B, an activator of BMP signaling, and a Wnt family member for a period of 1 day to 5 days, thereby generating DE cells.

In certain cases, PS cells may be cultured to produce DE cells in a differentiation medium that includes Activin A. In certain cases, PS cells may be cultured to produce DE cells in a differentiation medium that includes Activin A and Activin B. In certain cases, PS cells may be cultured to produce DE cells in a differentiation medium that includes Activin A, Activin B, and BMP4. The culturing may be carried out for 1 day to 6 days. In certain cases, the DE cells are generated from PS cells as described in U.S. Pat. No. 8,216,836, which is herein incorporated by reference in its entirety.

In certain cases, DE cells may be obtained from PS cells by culturing PS cells for a period of 1 day to 6 days or more in a medium that includes one or more of Nodal, Activin A, Activin B. In certain cases, the culturing of the PS cells in the medium that includes one or more of Nodal, Activin A, Activin B may be carried out for 1 day, 2 days, 3 days, 4 days, 5 days, or 6 days, thereby generating PS cells.

In certain cases, DE cells may be obtained from PS cells by culturing PS cells in a medium that includes one or more of Nodal, Activin A, Activin B in combination with a Wnt family member for a period of 1 day to 5 days, such as, 1 day, 2 days, 3 days, 4 days, 5 days, or 6 days. In certain cases, the PS cells may be cultured in a medium that includes one or more of Nodal, Activin A, Activin B in combination with a Wnt family member for a period of 1 day or 2 days, after which the culturing is carried out in a medium that includes one or more of Nodal, Activin A, Activin B but does not include a Wnt family member. In certain cases, the PS cells may be cultured in a medium that includes one or more of Nodal, Activin A, Activin B in combination with a Wnt family member for a period of 1 day or 2 days, after which the culturing is carried out in a medium that includes one or more of Nodal, Activin A, Activin B but does not include a Wnt family member, where the culturing without the Wnt family member may be carried out for 2 days, after which an activator of retinoic acid receptor may be included in the medium and the culturing carried out for an additional day or two days in the presence of one or more of Nodal, Activin A, Activin B and the activator of retinoic acid receptor.

In certain cases, the DE cells obtained by differentiation of PS cells may express certain markers of DE cells. For example, the DE cells may express one or more of DE cell markers such as Sox17, Foxa2 (also known as HNF3B or HNF3β), GSC, M1XL1, and CXCR4. In addition, the DE cells generated by the methods described herein do not express markers of mesoderm cell fate or ectoderm cell fate. As such, the DE cells do not express Brachyury, MOX1, Sox1, or ZIC1. In addition, the DE cells of the method described herein do not express markers of extra-embryonic visceral endoderm. For example, the DE cells disclosed herein do not express visceral endoderm markers, such as, Sox 7. In certain cases, the DE cells produced by the methods disclosed herein are positive for expression one or more DE cell markers, such as, Sox17, Foxa2, GSC, M1XL1, and CXCR4 and express no or low levels of AFP, SPARC, thrombomodulin, and Sox7.

Stage 2: Culturing of DE Cells to Produce AFE Cells

As noted above, a method for generating thymic epithelial progenitor (TEP) cells in vitro is provided. In certain embodiments, the method includes culturing definitive endodermal (DE) cells obtained from pluripotent stem cells in a medium that includes an activator of retinoic acid receptor, an activator of bone morphogenetic protein (BMP) signaling and an inhibitor of transforming growth factor-β (TGF-β) signaling to produce AFE cells.

The culturing may be carried out for 1 day to 6 days or more. For example, the culturing of DE cells may be carried out for 2-6 days, 1-5 days, 1-3 days, 2-5 days, 2-4 days, 2-3 days, 1 day, 2 days, 3 days, 4 days, 5 days, or 6 days.

In certain embodiments, the medium for culturing DE cells to produce TEP cells may not include Nodal or activins, such as Activin-A (ActA) or Activin-B (ActB).

The AFE cells produced by the methods described herein may express one or more markers of AFE cells. For example, the AFE cells produced by the methods described herein may express Sox 2, Foxa2 and/or Hhex. In addition, the AFE cells produced by the methods described herein may not express the posterior foregut endoderm marker Cdx2.

Stage 3: Culturing of AFE Cells to Produce VPE Cells

In certain embodiments, the production of TEP cells from DE cells may include an intermediate stage of production of VPE cells from the AFE cells by the above mentioned culturing of AFE cells.

As such, VPE cells may be produced by culturing the AFE cells in a medium that contains an activator of RA receptor, an activator of BMP signaling, an inhibitor of TGF-β signaling, as described above.

In certain cases, the method of producing TEP cells may further include culturing AFE cells produced by the culturing of the DE cells, where the culturing of the AFE cells is in a medium comprising an activator of of RA receptor, an activator of BMP signaling, and an inhibitor of TGF-β signaling and one or more of a Wnt family member, a fibroblast growth factor, and an inhibitor of hedgehog signaling. In certain cases, the medium may include an activator of RA receptor, an activator of BMP signaling, an inhibitor of TGF-β signaling, a Wnt family member, a fibroblast growth factor, and an inhibitor of hedgehog signaling.

The AFE cells may be cultured in the medium described above for a period of about 1 day to 8 days (e.g., 1-7 days, 1-5 days, 1-3 days, 2-7 days, 2-5 days, 2-4 days, 2-3 days, 1 day, 2 days, 3 days, 4 days, 5 days, 6 days, 7 days, or 8 days) to produce VPE cells.

The VPE cells produced by the methods described herein may express one or more markers of VPE cells, such as, Hoxa3, Pax1, or Eya1.

Stage 4: Culturing of VPE Cells to Produce TEP Cells

The method of producing TEP cells from DE cells produced from PS cells may further include culturing of VPE cells produced by the culturing of the AFE cells, where the culturing of the VPE cells is in a medium comprising an activator of RA receptor and an activator of BMP signaling.

In certain cases, the medium for generating thymic epithelial progenitor (TEP) cells from VPE cells produced by the culturing of the AFE cells may include an activator of RA receptor, an activator of BMP signaling, and one or more of a Wnt family member, a fibroblast growth factor, and an inhibitor of hedgehog signaling.

In certain cases, the medium for generating thymic epithelial progenitor (TEP) cells from VPE cells produced by the culturing of the AFE cells may include an activator of RA receptor, an activator of BMP signaling, a Wnt family member, a fibroblast growth factor, and an inhibitor of hedgehog signaling.

In certain cases, the VPE cells may be cultured in the medium for a period of about 1 day to about 10 days, where the VPE cells differentiate into TEP cells. In certain cases, the VPE cells may be cultured in the medium for 1 day to 10 days (e.g., 1-7 days, 1-5 days, 1-3 days, 2-7 days, 2-5 days, 2-4 days, 2-3 days, 1 day, 2 days, 3 days, 4 days, 5 days, 6 days, 7 days, 8 days, 9 days, or 10 days) to produce TEP cells.

The TEP cells produced by the methods described herein express markers of TEP cells, which markers are present in TEP cells present in thymus or thymic tissue, such as, adult human thymus or fetal human thymus. For example, TEP cells produced by the methods described herein may express the TEP markers at a level similar to the level expressed by cells in adult or fetal thymus. In certain cases, the TEP cells produced by the methods described herein express one or more of Foxn1, Hoxa3, Eya1, and EpCAM. In certain cases, the TEP cells produced by the methods provided herein express Foxn1 and Hoxa3. In certain cases, the TEP cells produced by the methods provided herein express Foxn1, Hoxa3, Pax1, EpCAM, and Eya1.

As such, a method for producing TEP cells from VPE cells by culturing the VPE cells in a medium containing one or more of an activator of RA receptor, an activator of BMP signaling, a Wnt family member, a fibroblast growth factor, and an inhibitor of hedgehog signaling for a period of about 1 day-10 days is provided.

In certain embodiments, the VPE cells may be produced as described above by culturing of AFE cells in a medium comprising one or more of an activator of RA receptor, an activator of BMP signaling, an inhibitor of TGF-β signaling, a Wnt family member, a fibroblast growth factor, and an inhibitor of hedgehog signaling for a period of about 1 day-8 days.

In certain embodiments, the AFE cells may be produced as described above by culturing of DE cells in a medium containing one or more of an activator of RA receptor, an activator of BMP signaling, an inhibitor of TGF-β signaling for a period of 1 day to 6 days.

In certain embodiments, the DE cells may be produced as described above by culturing of PS cells in a medium containing one or more of Nodal, Act-A, Act-B for a period of 1 day to 6 days.

In certain embodiments, the TEP cells may be generated within about 15 days (e.g., within 15 days-10 days, within 14 days-10 days, within 13 days-10 days, within 12 days-10 days, within 11 days-10 days, such as within 15 days, 14 days, 13 days, 12 days, 11 days, or 10 days) from the start of the culturing of the PS cells (e.g., pPS, such as, primate iPS cells, primate ES cells, human PS, human iPS cells, human ES cells). In certain embodiments, the method includes culturing the PS cells according to the methods described herein for about 1-5 days, e.g., 4 days-5 days to produce DE cells. In certain embodiments, the method further includes culturing the DE cells (produced from the PS cells) according to the methods described herein, for about 1-3 days e.g., 2-3 days (or till day 4-7, e.g., day 5-7 from the start of the culturing of the PS cells) to produce AFE cells. In certain embodiments, the method further includes culturing the AFE cells (produced from the DE cells) according to the methods described herein, for about 1-3 days e.g., 2-3 days (or till day 6-10, e.g., day 7-9 from the start of the culturing of the PS cells) to produce VPE cells. In certain embodiments, the method further includes culturing the VPE cells (produced from the AFE cells) according to the methods described herein, for about 1-3 days e.g., 2-3 days (or till day 10-15, e.g., day 10-12 or day 10-11 from the start of the culturing of the PS cells) to produce TEP cells.

The culturing methods described herein may be carried out in adherent conditions or in non-adherent conditions (e.g., suspension cultures). In some embodiments, the cell populations disclosed herein are cultured as an adherent culture.

The PS cells may be from any source. In certain cases, the PS cell may be embryonic stem cell, embryonic germ cells, and induced pluripotent stem cell. In certain cases, the PS cells may be primate pluripotent stem cells (pPS) cells. In certain cases, the pPS cells may be human pluripotent stem (hPS) cells. In certain cases, the hPS cells may be human embryonic stem (hES) cells. The hPS cells may be induced pluripotent stem (iPS) cells. In certain cases, the PS cell may be an established stem cell line. In certain cases, the PS cell may be an established embryonic stem cell line. In certain cases, the PS cell may be an established embryonic stem cell line, which cell line is derived from a blastomere generated by single blastomere biopsy (SBB) involving removal of a single blastomere from the eight cell stage of a developing organism. In certain embodiments, the PS cell may be an established stem cell line that does not include PS cells or ES cells produced by disaggregating human embryo or human blastocyst.

As noted above, the cell culture medium may include additives or supplements. In certain cases, the cell culture medium may not include serum. In certain cases, the cell culture medium may not include serum but may include serum replacement, such as KSR or B27. The type of cell culture medium and the additives for the cell culture medium may be different for certain differentiation stages of the cell populations.

In certain embodiments, the medium used for the culturing methods described herein may contain reduced serum or no serum. Serum concentrations can range from about 0.05% (v/v) to about 20% (v/v). For example, in certain embodiments, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some embodiments, the cells are grown without serum. In other embodiments, the medium used for the culturing methods described herein may contain no serum and may contain a serum replacement.

In still other embodiments, the medium used for the culturing methods described herein may contain B27 or KSR. In such embodiments, KSR or B27 can be provided to the culture medium in concentrations ranging from about 0.1% (v/v) to about 20% (v/v) or in concentrations greater than about 20% (v/v). In certain embodiments, the concentration of B27 or KSR in the medium is about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 15% (v/v) or about 20% (v/v).

In certain cases, RPMI 1640 media may be used for stages 1 and 2 while DMEM/F12 may be used for stages 3 and 4. In certain cases, RPMI 1640 media supplemented with increasing concentrations of KSR (0% on day 1 of culturing, 0.2% on day 2-day 3 of culturing, and 2% on day 4 of culturing) or 0.5% of B27 for day 5-day 7 of culturing may be used. In certain cases, DMEM/F12 with 0.5% B27 may be used for stages 3 and 4 of culturing.

Differentiation Factors

The methods and compositions of the present disclosure involve the use of various differentiation factors. Examples of differentiation factors used in the methods and compositions of the present disclosure are described below.

Activator of RA Receptor

An activator of RA receptor (RAR) may be a molecule capable of activating one or more of RARs, RAR-alpha, RAR-beta, and RAR-gamma. In certain cases, the activator may be a ligand for RA receptor. Examples of ligands of RA receptor include retinoids, such as, retinol, retinal, retinoic acid, all-trans retinoic acid, 9-cis-retinoic acid, etretinate, tazarotene, bexarotene, adapalene, TTNPB, DTAB (3-[(4,6-diphenoxy-1,3,5-triazin-2-yl)amino]benzoicacid), or a derivative or analog thereof.

In some embodiments of the methods and compositions described herein, an activator of RA receptor is provided to the cells in a medium such that it is present at a concentration of at least about 0.01 µM, at least about 0.03 µM, at least about 0.1 µM, at least about 0.2 µM, at least about 0.25 µM, at least about 0.3 µM, at least about 1 µM, at least about 1.3 µM, at least about 1.5 µM, at least about 2 µM, at least about 2.3 µM, at least about 2.5 µM, at least about 2.8 µM, at least about 3 µM, at least about 3.5 µM, at least about 4 µM, at least about 4.5 µM, at least about 5 µM, at least about 10 µM, at least about 20 µM, at least about 30 µM, at least about 40 µM or at least about 50 µM.

In certain cases, the activator for RA receptor may be present at different concentrations at different stages of the method for producing TEP cells. In certain cases, the activator for RA receptor may be present at a higher concentration during the generation of DE cells (Stage I) and/or AFE cells (Stage 2) than the concentration in a medium for generating VPE cells (Stage 3) and/or TEP cells (Stage 4).

In certain cases, the activator for RA receptor may be present in the medium used for generating DE cells and in a medium for generating AFE cells at a concentration of about at least about 0.2 µM, at least about 0.25 µM, at least about 0.3 µM, at least about 1 µM, at least about 1.3 µM, at least about 1.5 µM, at least about 2 µM, at least about 2.3 µM, at least about 2.5 µM, at least about 2.8 µM, or at least about 3 µM.

In some case, the activator of RA receptor may be a ligand for RA receptor. In certain cases, a ligand for RA receptor may be all-trans retinoic acid (RA). In certain cases, all trans-retinoic acid may be present at a concentration of 0.25 µM in a cell culture medium used for generating DE cells and in a cell culture medium used for generating AFE cells.

In certain cases, the ligand for RA receptor may be present in the medium used for generating VPE cells and/or TEP cells at a concentration of at least about 0.01 µM, at least about 0.03 µM, at least about 0.1 µM, or at least about 0.15 µM. In certain cases, a ligand for RA receptor may be all-trans retinoic acid (RA). In certain cases, all trans-retinoic acid may be present at a concentration of 0.1 µM in a cell culture medium used for generating VPE cells and in a cell culture medium used for generating TEP cells.

Fibroblast Growth Factor

In certain embodiments of the methods and compositions described herein, one or more differentiation factors of the fibroblast growth factor family, referred to herein generally as a "fibroblast growth factor" or "FGF", may be present in the medium used for cell culture. For example, in some embodiments, a fibroblast growth factor can be present in the medium, used for culturing cells, at a concentration of at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml, for example, at a concentration of at least 10 ng/ml, at least 25 ng/ml, at least 50 ng/ml, at least 75 ng/ml, at least 100 ng/ml, at least 200 ng/ml, at least 300 ng/ml, at least 400 ng/ml, at least 500 ng/ml, or at least 1000 ng/ml. In some embodiments, the FGF is present in the cell culture medium at a concentration of 10 ng/ml to 100 ng/ml, such as 20 ng/ml to 100 ng/ml, or 30 ng/ml to 100 ng/ml.

In certain embodiments, the FGF may be FGF2, FGF4, FGF7, FGF8a, FGF8b, FGF9, FGF10, or a variant thereof.

In certain embodiments, the FGF may be present in a medium used for the generation of VPE cells and/or TEP cells. In certain embodiments, the FGF may be present in a medium used for the generation of VPE cells and/or TEP cells may be FGF8 or FGF8b. In certain embodiments, the FGF may be present in a medium used for the generation of VPE cells and/or TEP cells may be FGF8b, which may be present at a concentration of 50 ng/ml.

Nodal, Activin A, and Activin B

In some embodiments, one or more differentiation factors such as Nodal, and/or Activin A, and/or Activin B or variants thereof or functional analogs thereof can be present in the medium for cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml, such as, about 10-500 ng/ml, 25 ng/ml-250 ng/ml, 50 ng/ml-200 ng/ml.

In some embodiments, one or more differentiation factors such as Nodal, and/or Activin A, and/or Activin B or variants or functional analogs thereof can be present in the medium for generation of DE cells from PS cells (stage 1). In some cases, the medium for generation of DE cells from PS cells (stage 1) may include Act-A at a concentration of 100 ng/ml.

Functional analogs of Activin-A include small molecules, IDE1 (2-[6-carboxy-hexanoyl)-hydrazonomethyl]-benzoic acid), IDE2 (7-(2-cyclopentylidenehydrazino)-7-oxoheptanoic acid described in Borowial M. et al. Cell Stem Cell 4, 348-358, Apr.; 3, 2009.

Wnt Family Members

In certain embodiments of the methods and compositions described herein, one or more differentiation factors of the Wnt family may be present in the medium used for cell culture. For example, in some embodiments, a Wnt family member can be present in the medium, used for culturing cells, at a concentration of at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml, for example, at a concentration of at least 10 ng/ml, at least 25 ng/ml, at least 50 ng/ml, at least 75 ng/ml, at least 100 ng/ml, at least 200 ng/ml, at least 300 ng/ml, at least 400 ng/ml, at least 500 ng/ml, or at least 1000 ng/ml. In some embodiments, the Wnt family member is present in the cell culture medium at a concentration of 5 ng/ml to 100 ng/ml, such as 10 ng/ml to 75 ng/ml, or 15 ng/ml to 50 ng/ml.

In certain cases, the Wnt family member may be present at different concentrations at different stages of the method for producing TEP cells. In certain cases, the Wnt family member may be present at a lower concentration during the generation of DE cells than the concentration in a medium for generating TEP cells. In certain cases, the Wnt family member may be Wnt3a that may be present at a concentration of 25 ng/ml in a cell culture medium used for differentiation of PS cell. In certain cases, the Wnt family member may be Wnt3a that may be present at a concentration of 50 ng/ml in a cell culture medium used for differentiation of AFE cells and for differentiation of VPE cells to produce TEP cells.

In certain cases, the Wnt family member may be an inducer of canonical Wnt signaling. In certain embodiments, the Wnt family member may be Wnt3a or a variant thereof which mediates canonical Wnt signaling. In certain cases, the Wnt family member may be Wnt/beta-catenin pathway agonists, such as, glycogen synthase kinase 3 beta (GSK3b) inhibitors, or casein kinase 1 (CK1) inhibitors. Non-limiting examples of Wnt agonists include DNA encoding β-catenin (e.g., naked DNA encoding β-catenin, plasmid expression vectors encoding β-catenin, viral expression vectors encoding β-catenin), β-catenin polypeptides, one or more Wnt/β-catenin pathway agonists (e.g., Wnt ligands, DSH/DVL-1, -2, -3, LRP6N, WNT3A, WNT5A, and WNT3A, 5A), one or more glycogen synthase kinase 3 β (GSK3 (3) inhibitors (e.g., lithium chloride (LiCl), Purvalanol A, olomoucine, alsterpaullone, kenpaullone, benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-dibenzyl-5-oxothiadiazolidine-3-thione (OTDZT), (2'Z,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N'-(5-nitro-1,3-thiazol-2-yl) urea (AR-A014418), indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5,5'-dibromoindirubin; 5-nitroindirubin; 5-chloroindirubin; 5-methylindirubin, 5-bromoindirubin, 4-Benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-Dibenzyl-5-oxothiadiazolidine-3-thione (OTDZT), (2'Z,3'E)-6-Bromoindirubin-3'-oxime (BIO), a-4-Dibromoacetophenone (i.e., Tau Protein Kinase I (TPK I) Inhibitor), 2-Chloro-1-(4,5-dibromo-thiophen-2-yl)-ethanone, (vi) N-(4-Methoxybenzyl)-N'-(5-nitro-1,3-thiazol-2-Aurea (AR-A014418), H-KEAPPAPPQSpP-NH2 (L803) and Myr-N-GKEAPPAPPQSpPNH2 (L803-mts)), one or more anti-sense RNA or siRNA that bind specifically to GSK3β mRNA, one or more casein kinase 1 (CK1) inhibitors (e.g., antisense RNA or siRNA that binds specifically to CK1 mRNA).

Activator of BMP Signaling

In certain embodiments of the methods and compositions described herein, one or more differentiation factors, such as, an activator of BMP signaling may be present in the medium used for cell culture. For example, in some embodiments, an activator of BMP signaling can be present in the medium, used for culturing cells, at a concentration of at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml, for example, at a concentration of at least 10 ng/ml, at least 25 ng/ml, at least 50 ng/ml, at least 75 ng/ml, at least 100 ng/ml, at least 200 ng/ml, at least 300 ng/ml, at least 400 ng/ml, at least 500 ng/ml, or at least 1000 ng/ml. In some embodiments, the activator of BMP signaling is present in the cell culture medium at a concentration of 5 ng/ml to 100 ng/ml, such as 10 ng/ml to 75 ng/ml, or 25 ng/ml to 75 ng/ml.

In certain embodiments, the activator of BMP signaling may be BMP1, BMP2, BMP3, BMP4, BMP5, BMP6, BMP7, BMP8a, BMP8b, BMP9/GDF, BMP10, BMP11/GDF11, BMP12/GDF7, BMP13/GDF6, BMP14/GDF5, BMP15/GDF9B, and variants thereof. In certain embodiments, the activator of BMP signaling may be BMP4 or a variant or a functional analog thereof.

Inhibitors of TGF-β Signaling

In certain embodiments of the methods and compositions described herein, an inhibitor of TGF-β signaling may be present in the medium for culturing cells. The inhibitor of TGF-β signaling may be present at a concentration of at least about 0.01 μM, at least about 0.03 μM, at least about 0.1 μM, at least about 0.2 μM, at least about 0.25 μM, at least about 0.3 μM, at least about 1 μM, at least about 1.3 μM, at least about 1.5 μM, at least about 2 μM, at least about 2.3 μM, at least about 2.5 μM, at least about 2.8 μM, at least about 3 μM, at least about 3.5 μM, at least about 4 μM, at least about 4.5 μM, at least about 5 μM, at least about 10 μM, at least about 20 μM, at least about 30 μM, at least about 40 μM or at least about 50 μM, such as, 0.5 μM-50 μM, 1 μM-25 μM, or 1 μM-10 μM.

In certain embodiments, the inhibitor of TGF-β signaling may be an antibody or a fragment thereof that binds to TGF-β1, TGF-β2, TGF-β3, TGF-β receptor I and/or II. In certain embodiments, the inhibitor of TGF-β signaling may be a small molecule inhibitor. In certain cases, the inhibitor of TGF-β signaling may be LY364947 (SD208), SM16, SB-505124, ALK5 Inhibitor II, or SB-431542. In general, the inhibitor of TGF-β signaling used in the method and compositions disclosed herein does not inhibit Nodal, Activin and/or BMP signaling.

Inhibitors of Hedgehog Signaling

In certain embodiments of the methods and compositions described herein, an inhibitor of hedgehog signaling may be present in the medium for culturing cells. The inhibitor of hedgehog signaling may be present at a concentration of at least about 0.01 μM, at least about 0.03 μM, at least about 0.1 μM, at least about 0.2 μM, at least about 0.25 μM, at least about 0.3 μM, at least about 1 μM, at least about 1.3 μM, at least about 1.5 μM, at least about 2 μM, at least about 2.3 μM, at least about 2.5 μM, at least about 2.8 μM, at least about 3 μM, at least about 3.5 μM, at least about 4 μM, at least about 4.5 μM, at least about 5 μM, at least about 10 μM, at least about 20 μM, at least about 30 μM, at least about 40 μM or at least about 50 μM, such as, 0.05 μM-5 μM, 0.01 μM-2.5 μM, 0.05 μM-1 μM, or 0.1 μM-1 μM.

In certain embodiments, the inhibitor of hedgehog (Hh) signaling may be an inhibitor of sonic hedgehog (Shh) signaling, desert hedgehog homolog (Dhh) signaling, and/or Indian hedgehog homolog (Ihh) signaling. In certain cases, the inhibitor of hedgehog signaling may be an inhibitor of sonic hedgehog signaling. In certain cases, the inhibitor of hedgehog signaling may be a small molecule. In certain cases, the inhibitor of hedgehog signaling may be a small molecule such as, CUR61414, IPI-926, (Saridegib), IPI-269609, cyclopamine, Vismodegib, or Erismodegib, or derivatives and analogs thereof.

Assessing Generation of Cell Populations

In certain cases, the cell populations cultured according to the methods disclosed herein may be monitored to assess changes in the cells imparted by culturing (e.g., during a stage of the culture method disclosed herein) so as to characterize the cell population produced. In certain embodiments, the production of DE cells, AFE cells, VPE cells, and/or TEP may be assessed by determining the expression of markers characteristic of these cell populations.

In certain cases, the expression of certain markers is determined by detecting the presence or absence of the marker. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest. In certain processes, the expression of marker genes characteristic of the cell population of interest as well as the lack of significant expression of marker genes characteristic of PS cells and other cell types may be determined.

Monitoring of generation of DE cells may be by determining expression of SOX17 gene. As such, the definitive endoderm cells produced by the processes described herein express the SOX17 marker gene, thereby producing the SOX17 gene product. The DE cells produced by the methods described herein also express the Foxa2 gene. Other markers of definitive endoderm include CXCR4, MIXL1, GATA4, HNF3b, GSC, FGF17, VWF, CALCR, FOXQ1, CMKOR1 and CRIP1. Since definitive endoderm cells express the SOX17 marker gene at a level higher than that of the SOX7 marker gene, which is characteristic of primitive and visceral endoderm, in some cases, the expression of both SOX17 and SOX7 may be monitored. In other embodiments, expression of the both the SOX17 marker gene and the OCT4 marker gene, which is characteristic of hESCs, may be monitored. Additionally, because definitive endoderm cells express the SOX17 marker gene at a level higher than that of the AFP, SPARC or Thrombomodulin (TM) marker genes, the expression of these genes can also be monitored.

As such, in some embodiments described herein, the expression of the SOX17 marker and/or the CXCR4 marker in definitive endoderm cells or cell populations is at least about 2-fold higher to at least about 10,000-fold higher than the expression of the SOX17 marker and/or the CXCR4 marker in non-definitive endoderm cells or cell populations, for example pluripotent stem cells. In other embodiments, the expression of the SOX17 marker and/or the CXCR4 marker in definitive endoderm cells or cell populations is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the SOX17 marker and/or the CXCR4 marker in non-definitive endoderm cells or cell populations, for example pluripotent stem cells.

Markers and methods for identifying DE cells or cell populations are described in U.S. Pat. No. 8,216,836, which is herein incorporated by reference in its entirety.

As noted above, monitoring of generation of AFE cells may be performed by determining expression of Sox 2. Monitoring of generation of VPE cells may be performed by determining expression of Hoxa3 or Eya1. Monitoring of generation of TEP cells may be carried out by determining Foxn1, Hoxa3, Eya1, and EpCAM.

In certain cases, the monitoring of generation of DE cells, AFE cells, VPE cells, and/or TEP cells may be carried out by performing functional analysis of the cells of interest. For example, TEP cells generated by the methods described herein may be functional. Functional TEP cells may generate thymic epithelial (TE) cells in vivo or in vitro. In certain cases, functional TEP cells produced by the methods disclosed herein may generate functional TE cells that support T cell development in vivo or in vitro.

In certain cases, the method does not include monitoring of generation of DE cells, AFE cells, VPE cells, and/or TEP cells.

Enrichment, Isolation and/or Purification of Cell Populations

Cell populations of interest, such as, DE cells, AFE cells, VPE cells, and/or TEP cells produced by any of the above-described processes can be enriched, isolated and/or purified by using an affinity tag that is specific for such cells. Examples of affinity tags specific for a cell or cell population of interest include antibodies, ligands or other binding agents that are specific to a marker molecule, such as a polypeptide, that is present on the cell surface of the cells of interest but which is not substantially present on other cell types that may be found in a cell culture produced by the methods described herein.

Methods for making antibodies and using them for cell isolation are known in the art and such methods can be implemented for use with the antibodies and cells described herein. In one process, an antibody which binds to a marker expressed by cell population of interest is attached to a magnetic bead and then allowed to bind to the cells of interest in a cell culture which has been enzymatically treated to reduce intercellular and substrate adhesion. The cell/antibody/bead complexes are then exposed to a magnetic field which is used to separate bead-bound definitive endoderm cells from unbound cells. Once the cells of interest are physically separated from other cells in culture, the antibody binding is disrupted and the cells are replated in appropriate tissue culture medium.

Additional methods for obtaining enriched, isolated, or purified cell populations of interest can also be used. For example, in some embodiments, an antibody for a marker expressed by the cells of interest is incubated cell culture containing the cells of interest that has been treated to reduce intercellular and substrate adhesion. The cells are then washed, centrifuged and resuspended. The cell suspension is then incubated with a secondary antibody, such as an FITC-conjugated antibody that is capable of binding to the primary antibody. The cells are then washed, centrifuged and resuspended in buffer. The cell suspension is then analyzed and sorted using a fluorescence activated cell sorter (FACS). Antibody-bound cells are collected separately from cells not bound to the marker specific antibody, thereby resulting in the isolation of cells of interest. If desired, the isolated cell compositions can be further purified by using an alternate affinity-based method or by additional rounds of sorting using the same or different markers that are specific for the cells of interest.

In certain cases, cells of interest, such as, DE cells, AFE cells, VPE cell, and/or TEP cells are enriched, isolated and/or purified from other types of cells after the PS cell cultures are induced to differentiate towards the TEP cell lineage. It will be appreciated that the above-described enrichment, isolation and purification procedures can be used with such cultures at any stage of differentiation.

In addition to the above-described procedures, cells of interest, such as, TEP cells may also be isolated by other techniques for cell isolation. Additionally, cells of interest, such as TEP cells, may also be enriched or isolated by methods of serial subculture in growth conditions which promote the selective survival or selective expansion of the cells of interest.

Using the methods described herein, cell populations or cell cultures enriched in cells of interest, such as, TEP cells, by at least about 2- to about 1000-fold as compared to un-enriched cell populations are produced. In some embodiments, DE cells, and/or AFE cells, and/or VPE cells, and/or TEP cells can be enriched by at least about 5- to about 500-fold as compared to untreated cell populations or cell cultures. In other embodiments, DE cells, and/or AFE cells, and/or VPE cells, and/or TEP cells can be enriched from at least about 10- to about 200-fold as compared to untreated cell populations or cell cultures. In still other embodiments, DE cells, and/or AFE cells, and/or VPE cells, and/or TEP cells can be enriched from at least about 20- to about 100-fold as compared to untreated cell populations or cell cultures. In yet other embodiments, DE cells, and/or AFE cells, and/or VPE cells, and/or TEP cells can be enriched from at least about 40- to about 80-fold as compared to untreated cell populations or cell cultures. In certain embodiments, DE cells, and/or AFE cells, and/or VPE cells, and/or TEP cells can be enriched from at least about 2- to about 20-fold as compared to untreated cell populations or cell cultures.

Genotypic Features of Cell Populations of the Present Disclosure

When derived from an isolated PS cell, or an established line of PS cells, the cell populations of this disclosure can be characterized as being the progeny of the originating cell or cell line. Accordingly, the cell populations will have the same genome as the cells from which they are derived. This means that over and above any karyotype changes, the chromosomal DNA will be over 98% (e.g., at least 98.5%, 98.8%, 99%, 99.3%, 99.5%, 99.9%, or more) identical between the PS cells and the cell populations generated therefrom. Cell populations of the present disclosure that have been treated by recombinant methods to introduce a transgene or knock out an endogenous gene are still considered to have the same genome as the line from which they are derived, since all non-manipulated genetic elements are preserved. Cell populations of the present disclosure and PS cells can be identified as having the same genome by standard genetic techniques. Possession of the same genome can also be inferred if the cell populations are obtained from the undifferentiated line through the course of normal mitotic division.

In certain industrial applications, this characteristic is a valuable feature of the cell populations of the present disclosure. In particular, the availability of the originating PS cells provides a further supply of genetically matched differentiated cell populations, since the PS cells can be caused to proliferate and differentiated into more cell populations of the present disclosure as required. Furthermore, the PS cells can be differentiated into other therapeutically important lineages.

The techniques described in this application allow for the production of large cell populations that share the same genome, by expanding the cells before or after differentiation. Populations of $10^8$, $10^{10}$, or $10^{12}$ cells are theoretically possible. Such large populations are usually divided into separate containers suitable for further culture, drug screening, or therapeutic administration.

Certain embodiments of the disclosure include originating cells (such as a undifferentiated PS cell line, or an intermediate population, e.g., DE cells, AFE cells, VPE cells) in combination with one or more populations of differentiated cells bearing characteristics of DE cells, AFE cells, VPE cells, or TEP cells. The populations may either be in the same container, in separate containers in the same facility, or in two different locations. The undifferentiated and differentiated cells may be present simultaneously or at a different time, such as when a culture of undifferentiated cells is caused to differentiate into TEP cells, as described herein.

Compositions and Systems Comprising Cell Populations of the Present Disclosure

Cell Compositions

Cell compositions produced by the above-described methods include cell cultures that contain isolated TEP cells and cell populations enriched in isolated TEP cells. In certain cases, the cell composition including isolated TEP cells may further include one or more of an activator of RA receptor, an activator of BMP signaling, a Wnt family member, a fibroblast growth factor, and an inhibitor of hedgehog signaling.

In general, the TEP cells of the present disclosure present in the systems, cell populations, and compositions described herein are functional. In certain embodiments, the TEP cells are functional and further differentiate into TE cells under appropriate conditions, in vivo or in vitro. The functional activity of the TEP cells may be assessed by any of the methods described herein or any of the art accepted methods, such as, those described in Inami Y. et al., Immunology and Cell Biology (2011) 89, 314-321; Lai L. and Jin J., Stem Cells. 2009 Dec.; 27(12):3012-20; Lai L. et al., Blood. 2011 Sep. 22; 118(12):3410-8. For example, the functional TEP cells may further mature upon transplantation into functional TE cells that support T cell development.

In certain embodiments, the TEP cells of the present disclosure present in the systems, cell populations, and compositions described herein express one or more of markers of TEP cells, which markers are present in TEP cells present in thymus or thymic tissue, such as, adult human thymus or fetal human thymus. For example, TEP cells produced by the methods described herein may express the TEP markers at a level similar to the level expressed by TEP cells in adult or fetal thymus. In certain cases, the TEP cells of the present disclosure express one or more of FOXN1, HOXA3, EYA1, GCM2, and EpCAM. In certain cases, the TEP cells produced by the methods provided herein express FOXN1. In certain cases, the TEP cells produced by the methods provided herein express HOXA3. In certain cases, the TEP cells produced by the methods provided herein express FOXN1 and HOXA3. In certain cases, the TEP cells produced by the methods provided herein express FOXN1, HOXA3, and EpCAM. In certain cases, the TEP cells produced by the methods provided herein express FOXN1, HOXA3, and EYA1. In certain cases, the TEP cells produced by the methods provided herein express FOXN1, HOXA3, PAX1, EpCAM, and EYA1. In certain cases, the TEP cells provided herein do not express significant levels of marker genes characteristic of mature TECs such as HLA-DRA (MHC class II molecule) and AIRE. Detection of expression of one or more of FOXN1, HOXA3, EYA1, GCM2, and EpCAM can be accomplished according to the methods known in the art, such as those discussed herein.

As such, the TEP cells of the present disclosure express one or more of the markers provided herein and are functional.

As noted herein the TEP cells of the present disclosure may be mammalian, e.g., primate TEP cells, such as, human TEP cells.

Cell compositions produced by the above-described methods include cell cultures that include isolated VPE cells and cell populations enriched in VPE cells. In certain cases, the cell composition containing VPE cell may include one or more of an activator of RA receptor, an activator of BMP signaling, a Wnt family member, a fibroblast growth factor, and an inhibitor of hedgehog signaling. In certain cases, the cell composition of VPE cells may include one or more of an activator of RA receptor, an activator of BMP signaling, an inhibitor of TGF-β signaling, a Wnt family member, a fibroblast growth factor, and an inhibitor of hedgehog signaling. In general, the VPE cells present in the cell populations are capable of differentiating into TEP cells, when cultured according to the methods disclosed herein.

Cell compositions produced by the above-described methods include cell cultures that include AFE cells and cell populations enriched in AFE cells. In certain cases, the cell composition comprising AFE cell may include one or more of an activator of RA receptor, an activator of BMP signaling, an inhibitor of TGF-β signaling, a Wnt family member, a fibroblast growth factor, and an inhibitor of hedgehog signaling. In general, the AFE cells present in the cell populations are capable of differentiating into VPE cells, and TEP cells, when cultured according to the methods disclosed herein.

Cell compositions produced by the above-described methods include cell cultures that include DE cells and cell populations enriched in DE cells. In certain cases, the cell composition comprising DE cell may include one or more of an activator of RA receptor, an activator of BMP signaling, and an inhibitor of TGF-β signaling. In certain cases, the cell composition comprising DE cell may include one or more of an activator of RA receptor, Nodal, Act-A, Act-B. In general, the DE cells present in the cell populations are capable of differentiating into AFE cells, VPE cells, and TEP cells, when cultured according to the methods disclosed herein.

In some embodiments, cell compositions which include cells of the present disclosure (e.g., TEP cells, or VPE cells, or AFE cells, or DE cells), wherein at least about 50%-80% of the cells in culture are the cells of interest, can be produced. The differentiation methods described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells to cells of interest.

In embodiments, in which isolation of cells of interest is employed, for example, by using an affinity reagent that binds to the cells of interest, a substantially pure cell population of interest can be recovered.

Some embodiments described herein relate to cell compositions comprising from at least about 5% cells of interest to at least about 95% cells of interest. In some embodiments, the cell cultures or cell populations comprise mammalian cells. In preferred embodiments, the cell cultures or cell populations comprise human cells. For example, certain specific embodiments relate to cell compositions comprising human cells, wherein from at least about 5% to at least about 95% of the human cells are TEP cells. Other embodiments relate to cell compositions comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the human cells are TEP cells.

Cell compositions produced by the above-described methods and compositions thereof may be assessed by using the markers and methods described herein as well as those known in the art.

Cell compositions produced by the above-described methods and compositions thereof may be enriched, isolated or purified using methods described herein as well as those known in the art.

Cell compositions provided herein may be pharmaceutical compositions that include a pharmaceutically acceptable carriers. Examples of pharmaceutically acceptable carriers include saline, buffers, diluents, fillers, salts, stabilizers, solubilizers, cell culture medium, and other materials which are well known in the art. In some embodiments, the formulations are free of detectable DMSO (dimethyl sulfoxide).

For general principles in medicinal formulation of cell compositions, the reader is referred to Cell Therapy: Stem Cell Transplantation, Gene Therapy, and Cellular Immunotherapy, by G. Morstyn & W. Sheridan eds, Cambridge University Press, 1996; and Cell Transplantation for Neurological Disorders, T. B. Freeman et al. eds., Humana Press 1998. The cells may be packaged in a device or container suitable for distribution or clinical use, optionally accompanied by information relating to the storage of the cells or their use as a medicament to treat clinical conditions, or for any other worthwhile purpose.

Also provided herein is a first in vitro cell population including primate (e.g., human) pluripotent stem cells and a second in vitro cell population comprising progeny of a portion of the first in vitro cell population, wherein the progeny are TEP cells as described herein. Accordingly, the TEP cells in the second in vitro cell population may be functional and express the markers provided herein. For example, the TEP cells may express FOXN1 and HOXA3. The markers and functional activity of the TEP cells are described above.

The first and second in vitro cell populations may exist at the same time or at different times. The first and second in vitro cell populations may be present in the same container or in different containers.

In certain cases, the first in vitro cell population may be pPS cells, DE cells, AFE cells or VPE cell and the second in vitro cell population may be TEP cells, where the TEP cells are progeny of the pPS cells, DE cells, AFE cells or VPE cells.

In certain cases, the first in vitro cell population may be DE cells and the second in vitro cell population may be AFE cells, where the AFE cells are progeny of the DE cells.

The first in vitro cell population may be DE cells and the second in vitro cell population may be VPE cells, where the VPE cells are progeny of the DE cells.

The first in vitro cell population may be AFE cells and the second in vitro cell population may be VPE cells, where the VPE cells are progeny of the AFE cells.

Also provided herein is a first, second, and third in vitro cell populations, where the first cell population may be AFE cells, the second cell population may be VPE cells and the third cell population may be TEP cells, where the VPE cells are progeny of AFE cells and TEP cells are progeny of VPE cells.

Also provided herein is a first, second, third, and fourth in vitro cell populations, where the first cell population may be DE cells, the second cell population may be AFE cells, the third cell population may be VPE cells and the fourth cell population may be TEP cells, where the AFE cells are the progeny of DE cells, the VPE cells are progeny of AFE cells and TEP cells are progeny of VPE cells.

Also provided herein is a first, second, third, fourth, and fifth in vitro cell populations, where the first cell population may be pPS cells, the second cell population may be DE cells, the third cell population may be AFE cells, the fourth cell population may be VPE cells and the fifth cell population may be TEP cells, where the DE cells are progeny of the pPS cells, the AFE cells are the progeny of DE cells, the VPE cells are progeny of AFE cells and TEP cells are progeny of VPE cells.

Systems

Also provided herein is a system for efficient production of primate TEP cells for use in research or the preparation of pharmaceutical compositions for treatment of a subject in need of treatment with TEP cells.

The systems of the present disclosure include a set or combination of cells that exist at any time during manufacture, distribution, or use. The cell sets comprise any combination of two or more cell populations described in this disclosure, exemplified but not limited to a type of differentiated pPS-derived cell (such as, TEP cells, VPE cells, AFE cells, DE cells), in combination with undifferentiated pPS cells or other differentiated cell types, sometimes sharing the same genome. Each cell type in the set may be packaged together, or in separate containers in the same facility, or at different locations, at the same or different times, under control of the same entity or different entities sharing a business relationship.

In certain embodiments, a differentiated cell population as part of a system for generating TEP cells is provided. The TEP cells of the system have functional and phenotypic characteristics (e.g., expression of TEP cell markers) as provided herein and are the progeny of primate pluripotent stem (pPS) cells. In other words, the TEP cells of the system are produced by differentiation of pPS cells.

In exemplary embodiments, the system of components for generating TEP cells may include a line of undifferentiated human PS cells and a cell population of TEP cells differentiated therefrom, wherein the TEP cells express one or more of the TEP cell markers, such as those provided herein (e.g., FOXN1). For example, the system of components for generating TEP cells may include a line of undifferentiated human PS cells and a cell population of TEP cells differentiated therefrom, wherein the TEP cells are express FOXN1 and are negative for KRT1 and KRT10.

In exemplary embodiments, the system of components for generating TEP cells may include a cell population of human DE cells and a cell population of TEP cells differentiated therefrom, wherein the TEP cells express one or more of the TEP cell markers, such as those provided herein (e.g., FOXN1).

The system of components for generating TEP cells may include human AFE cells and a cell population of TEP cells differentiated therefrom, wherein the TEP cells express one or more of the TEP cell markers, such as those provided herein (e.g., FOXN1).

The system of components for generating TEP cells may include human VPE cells and a cell population of TEP cells differentiated therefrom, wherein the TEP cells express one or more of the TEP cell markers, such as those provided herein (e.g., FOXN1).

The system of components for generating TEP cells may include human PS cells and a cell population of DE cells differentiated therefrom, wherein the DE cells express one or more of the DE cell markers, such as those provided herein.

The system of components for generating TEP cells may include human PS cells and a cell population of AFE cells differentiated therefrom, wherein the AFE cells express one or more of the AFE cell markers, such as those provided herein.

The system of components for generating TEP cells may include human PS cells and a cell population of VPE cells differentiated therefrom, wherein the VPE cells express one or more of the VPE cell markers, such as those provided herein.

The system of components for generating TEP cells may include human PS cells, a cell population of DE cells differentiated from the PS cells, a cell population of AFE cells differentiated from the DE cells, cell population of VPE cells differentiated from the AFE cells, and a cell population of TEP cells differentiated from the AFE cells, wherein the cell populations express one or more markers typical for the particular cell, such as, those described herein.

The cell population of TEP cells of the system and compositions described herein may include at least 10%-95% or more TEP cells (e.g. 15%-90%, 20%-80%, 50%-70%, 10%, 20%, 30%, 40%, 50%, 60%, 70%, 80%, 90%, 95%, or 99%).

The cell population of VPE cells of the system and compositions described herein may include at least 10%-95% or more VPE cells (e.g. 15%-90%, 20%-80%, 50%-70%, 10%, 20%, 30%, 40%, 50%, 60%, 70%, 80%, 90%, 95%, or 99%).

The cell population of AFE cells of the system and compositions described herein may include at least 10%-95% or more AFE cells (e.g. 15%-90%, 20%-80%, 50%-70%, 10%, 20%, 30%, 40%, 50%, 60%, 70%, 80%, 90%, 95%, or 99%).

The cell population of DE cells of the system and compositions described herein may include at least 10%-95% or more DE cells (e.g. 15%-90%, 20%-80%, 50%-70%, 10%, 20%, 30%, 40%, 50%, 60%, 70%, 80%, 90%, 95%, or 99%).

Uses of Cell Populations of the Present Disclosure

Cell Populations for Screening

The cells of the present disclosure can be used to screen for agents (such as, small molecules, peptides, polynucleotides) or environmental conditions (such as, culture conditions or manipulation) that affect the characteristics of PS cells, DE cells, AFE cells, VPE cells, and/or TEP cells.

In one example, PS cells, DE cells, AFE cells, and/or VPE cells (undifferentiated or initiated into the differentiation paradigm) are used to screen factors that promote maturation into TEP cells, or promote proliferation and maintenance of TEP cells in long-term culture. For example, candidate differentiation factors or growth factors are tested by adding them to cells in different wells, and then determining any phenotypic change that results, according to desirable criteria for further culture and use of the cells. This can lead to improved derivation and culture methods for generating DE cells, AFE cells, VPE cells, and/or TEP cells.

Other screening methods of the present disclosure relate to the testing of pharmaceutical compounds for a potential adverse effect on TEP cells. This type of screening is appropriate not only when the compound is designed to have a pharmacological effect on TEP cells themselves, but also to test for TEP cells/TE cells-related side-effects of compounds designed for a primary pharmacological effect elsewhere.

Other screening methods relate to the use of TEP cells to measure the effect of small molecule drugs that have the potential to affect immune system. To this end, the cells can be combined with test compounds in vitro, and the effect of the compound on TEP cells is determined.

General principles of drug screening are described in U.S. Pat. No. 5,030,015, and in the textbook In vitro Methods in Pharmaceutical Research, Academic Press 1997. Assessment of the activity of candidate pharmaceutical compounds generally involves combining the differentiated cells of this invention with the candidate compound, either alone or in combination with other drugs. The investigator determines any change in the morphology, marker, or functional activity of the cells that is attributable to the compound (compared with untreated cells or cells treated with a negative control compound), and then correlates the effect of the compound with the observed change.

TEP Cells in Clinical Therapy

Cell populations comprising TEP cells, such as, cell populations enriched in TEP cells, as well as, purified TEP cells produced by the methods described herein may be used in a number of clinical applications.

In certain embodiments, the TEP cells produced using the methods provided herein may be used for generating functional thymic epithelial (TE) cells in a subject in need of TE cells.

A subject in need of TEP cells may be a subject having a genetic and/or developmental defect that results in reduced or undetectable thymus functions. In certain cases, the subject may have DiGeorge syndrome or complete DiGeorge syndrome. Complete DiGeorge syndrome is a fatal condition in which infants have no detectable thymus function. The TEP cells of the present disclosure find may be used for treatment of infants with complete DiGeorge syndrome. For example, infants with complete DiGeorge syndrome may be treated using the instant TEP cells by following the transplantation procedure described by Markert M. L. et al., Blood. 2003 Aug. 1; 102(3):1121-30. Epub 2003 Apr. 17.

In certain embodiments, the TEP cells produced using the methods provided herein may be used in thymus regeneration therapy.

The TEP cells may be transplanted into a subject in need of TE cells. In certain cases, the TEP cells may be transplanted into a target site in a subject that provides appropriate differentiation conditions for the TEP cells to differentiate into TE cells. Cells may be transplanted by any of a number of standard methods in the art for delivering cells to tissue, e.g., injecting them as a suspension in a suitable buffer (saline, PBS, DMEM, Iscove's media, etc. or a pharmaceutically acceptable carrier), providing them on a solid support, e.g. a bead, a filter such as a mesh filter, a membrane, etc. In certain cases, the TEP cells may be transplanted into the thymus of a subject. In certain cases, the TEP may be transplanted under the kidney capsule of a subject.

In certain cases, a subject in need of TEP cell transplantation may be a subject that needs an increase in enhancement or restoration of thymic function. In certain cases, the subject may be a subject whose thymus has undergone profound degeneration due to aging. In certain cases, the subject may be a subject whose thymus has undergone profound degeneration due to exposure to radiation. In certain cases, the subject may be a subject whose thymus has undergone profound degeneration due to chemotherapy.

TEPs generated from patient-specific induced pluripotent stem (iPS) cells lines may also be used as a tool to model human disease.

In certain cases, the TEPs generated by the method described herein may be genetically modified to express a protein of interest.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

Cell Culture.

Undifferentiated CyT49 and HUES4 hESCs were maintained on mitomycin treated mouse embryonic fibroblast (MEF) feeders (Millipore) as previously described (D'Amour et al., 2006). For differentiation, hESCs were plated on MEFs at a density of $6.25 \times 10^4$ cm$^2$ and differentiated 72 h later as follows: stage 1 and 2 of differentiation were carried out in RPMI 1640 media (Invitrogen) supplemented with increasing concentrations of KSR (0% on d1, 0.2% on d2-3 and 2% on d4) or B27 (0.5% on d5-7). For stage 3 and 4, cells were differentiated in DMEM/F12 with 0.5% B27. The following factors were added: Activin A 100 ng/ml (d1-5), Wnt3a 25 ng/ml (d1) or 50 ng/ml (d8-11), all-trans retinoic acid (RA) 0.25 µM (d4-7) or 0.1 µM (d8-11), BMP4 50 ng/ml (d6-11), LY364947 5 µM (d6-9), FGF8b 50 ng/ml (d8-11), KAAD-cyclopamine 0.5 µM (d8-11). Supplements and factors were from Invitrogen (B27, KSR), R&D Systems (activinA, Wnt3a, BMP4, FGF8b), Sigma (RA), and Millipore (KAAD-cyclopamine, LY364947). Two exemplary differentiation protocols for generation of TEP cells from ES cells are outlined in FIGS. 5 and 6.

Real-Time Quantitative PCR.

RNA extraction of hESC cultures was done using Nucleospin RNA II columns (E&K Scientific) or RNeasy micro kit (QIAGEN) according to the manufacturer's instructions. RNA extraction from dissected grafts was performed with TRIzol reagent (Invitrogen). RNA was reverse transcribed using iScript cDNA synthesis kit (Bio-Rad). cDNA from some of the dissected grafts was pre-amplified using a Taqman PreAmp kit (Applied Biosystems). Real-time quantitative PCR was performed on a 7900 HT Fast Real-Time PCR System (Applied Biosystems) using the human specific SYBR green primers or Taqman assays (Applied Biosystems) listed below. After normalization to the housekeeping gene TBP, samples were plotted relative to undifferentiated ES cells. Fetal and adult human thymus RNA samples were either extracted from fresh pieces of thymus (Advanced Bioscience Resources) or were purchased from Agilent and Clontech.

TABLE 1

Taqman gene expression assays used for real-time qPCR

| Gene | Gene expression assay |
|---|---|
| TBP | Hs00920494_m1 |
| FOXN1 | Hs00186096_m1 |
| HOXA3 | Hs00601776_m1 |
| EYA1 | Hs00166804_m1 |
| GCM2 | Hs00171702_m1 |
| HLA-DRA | Hs00219575_m1 |
| CCL25 | Hs00608373_m1 |
| CXCL12 | Hs00171022_m1 |
| SCF | Hs00241497_m1 |

TABLE 2

Sequences of primers used for real-time qPCR (SYBR Green)

| Gene | Forward primer | Reverse primer |
|---|---|---|
| TBP | TGTGCACAGGAGCCAAGAGT | ATTTTCTTGCTGCCAGTCTGG |
| FOXN1 | AGGCCTTCGAGGAGATCCCAGT | TCTCCAGAACTGGGGGCTTGACT |
| HOXA3 | G GCAGCTCCAGCTCAGGCAA | GCCGGCACAGGTAGCGGTTG |
| EYA1 | GCTTCAACGACAGCCGACGGG | AACTGGTGAGTTGGTCGTGGGC |
| GCM2 | CCCTAACTGTCATTCTGCTTTG | TGATTTGCTCTCTGGTCTTGGA |

Immunofluorescence.

hESC cultures were fixed for 15 min in PBS+4% paraformaldehyde, washed twice in PBS and blocked for 30 min in CAS-block (Invitrogen). Primary antibodies (listed below) and secondary antibodies (Alexa Fluor tagged secondary antibodies (Invitrogen), 1:500) were diluted in PBS+0.4% Triton X-100 and were incubated for 1 h at room temperature (RT). Nuclei were stained with 4',6-diamidino-2-phenylindole (DAPI). For tissue sections, kidneys were embedded in OCT medium (Tissue-Tek) and snap frozen. 10 µm sections cut using a cryostat were fixed in cold acetone for 10 min and dried at RT for one hour before storage at −80° C. or immediate staining Slides were washed three times in PBS and incubated in CAS-block (Invitrogen) for 30 minutes at RT. Primary antibodies (listed below) diluted in PBS+3% BSA were added directly to blocking solution on the tissue section and incubated for one hour at RT or overnight at 4° C. Slides were washed three times in PBS and then incubated with secondary antibodies (Alexa Fluor tagged secondary antibodies (Invitrogen), 1:500) in PBS+3% BSA for one hour at RT. Slides were washed three times in PBS before being mounted in Vectashield mounting medium containing DAPI (Vector Laboratories). Images were taken with Zeiss ApoTome and Leica SP5 microscopes or InCell Analyzer 2000 (GE Healthcare) for quantification. Nine fields from each well were picked randomly for quantification analysis and the percentage of total DAPI positive nuclei that were positive for Hoxa3 was determined using InCell Developer software.

TABLE 3

Primary antibodies used for immunofluorescence

| Antigen | Host species | Company | Catalog number | Dilution |
|---|---|---|---|---|
| Hoxa3 | Rabbit | Novus | NBP1-83234 | 1:350 |
| EpCAM | Mouse | Biolegend | 324201 | 1:200 |
| K5 | Rabbit | Abcam | ab53121 | 1:500 |
| K8 | Chicken | Abcam | ab107115 | 1:500 |
| wide spectrum cytokeratin | Rabbit | Abcam | ab9377 | 1:300 |
| CD4 (conjugated to AlexaFluor 647) | Rat | Biolegend | 100424 | 1:100 |
| CD8 (conjugated to FITC) | Rat | Biolegend | 100706 | 1:100 |
| CD3 | Rabbit | Abcam | ab5690 | 1:100 |
| Ki67 (conjugated to AlexaFluor 647) | Mouse | BD Biosciences | 561126 | 1:100 |

Kidney Capsule Implantations.

hESC cultures differentiated using condition 1 (control) or 7 (TEP) were either incubated with accutase for 5 min or cut into ~2 to 5-mm squares using a needle. Cell clumps were lifted with a cell scraper, collected by centrifugation, washed and resuspended in differentiation media +10 µg/ml DNAse I (Sigma). Following a 4-6 h incubation at 37° C., ~2-4×10$^6$ cells were implanted under the kidney capsule of nude mice as described (Russ and Efrat, 2011). HFT grafts were generated by implanting ~1-mm$^3$ piece of human fetal thymus under the kidney capsule of nude mice using a similar technique. Fresh human fetal thymus was obtained from Advanced Bioscience Resources. 4 to 22 weeks after transplantation, kidneys were surgically extracted and the tissue was processed for histology, RNA extraction or analysis by flow cytometry.

Flow Cytometry.

Cells isolated from thymic, dissected grafts, or spleens were treated with ACK lysis buffer for 5 min and were washed twice before blocking in FACS buffer (PBS+1% FBS+2 mM EDTA) with anti-Fc receptor blocking antibody (clone 2.4G2) (UCSF Monoclonal Antibody Core) for 15 min. Cells were then incubated with different combinations of fluorescein isothiocyanate (FITC)-, phycoerythrin (PE)-, allophycocyanin (APC)- or PE-Cy7-conjugated antibodies against mouse CD4 (GK1.5), mouse CD3 (145-2C11), mouse TCRβ (H57-597), mouse CD8 (53-6.7), mouse CD90.2 (53-2.1), and mouse Foxp3 (FJK-16s) for 30 minutes on ice before being washed with PBS. For intracellular staining of Foxp3, a FoxP3 staining kit (eBioscience) was used. Analysis was done using a LSRII cytometer (BD Biosciences) and FlowJo software (Tree Star). Data shown are after gating for lymphocytes with lightscatter parameters and exclusion of dead cells by staining with DAPI. Antibodies were from eBioscience and BioLegend.

Spectratyping.

Total RNA was isolated from 5 to 10×10$^6$ splenocytes using TRIzol reagent (Invitrogen) and RNeasy Mini columns (Qiagen) followed by reverse transcription into cDNA using SuperScript III first-strand synthesis system (Invitrogen). PCR and run-off reactions were performed using a common Cβ primer and primers specific for each TCR Vβ family as described previously (Currier and Robinson, 2001, Current Protocols in Immunology). Labeled products from the run-off reactions were analyzed using a 3130x1 GeneticAnalyzer (Applied Biosystems) and GeneMapper software (Applied Biosystems). The overall spectratype complexity score for each mouse was determined by counting the number of discrete peaks per Vβ subfamily, with each subfamily graded on a score of 0 to 5. Spectratypes containing more than 5 peaks were given a score of 5, while others were given a score from 0 to 4, according to the number of peaks obtained (Lu et al., 2004, Blood 103, 4588-4593).

Mix Lymphocyte Reaction (MLR).

T cells for the MLR assay were prepared from spleens harvested from donor mice (C57BL/6 MHC haplotype H2b or NU/J MHC haplotype H2q) that were mashed and strained through 70 µm filters. After ACK lysis, T cells were enriched with a Robosep T cell negative selection kit (cat #19751, Stemcell Technologies, Vancouver, Canada). Enriched T cells resuspended in DMEM/2% FBS were labeled with a solution of 5 µm CFSE for 5 min at RT. An equal volume of FBS was added to quench and cells were washed with DMEM/2% FBS. Cells were added to round-bottom 96-well plates at 2×10$^5$ cells per well in complete DMEM media. APCs for the MLR assay were prepared from spleens harvested from donor mice (NOD MHC haplotype H2 g7 or NU/J MHC haplotype H2q) into DMEM with 2% FBS, 0.125% Collagenase D (Roche), 100 ug/mL DNase (Roche), and 100 ug/mL Collagenase/Dispase (Roche). Following mincing, the tissues were incubated at 37° C. for one hour with periodic mixing. Digested tissue was pelleted and resuspended in AutoMACS buffer (1x PBS, 0.5% BSA, 2 mM EDTA). CD11c+ DCs were positively selected with a Robosep kit (cat #18758) according to the manufacturer's instructions. Enriched DCs were added to wells at 2×10$^4$ cells per well. After 4 days of culture, loss of CFSE in CD4+ and CD8+ T cells was assayed by staining with anti-CD90.2, anti-CD4 and anti-CD8 antibodies and analyzing by flow cytometry.

Proliferation Assay.

10$^7$ splenocytes were labeled with a solution of 5 µm CFSE diluted in DMEM+2% FBS for 5 min at RT. An equal volume of FBS was added and cells were washed with DMEM+2% FBS. CFSE labeled-cells were then cultured in round bottom 96-well plates pre-coated with anti-CD3 and anti-CD28 antibodies (10 µg/ml) at a cell density of 4×10$^5$ cells/well. After 3 days, loss of CFSE in CD4+ and CD8+ T cells was assayed by staining with anti-CD4 and anti-CD8 antibodies and analyzing by flow cytometry.

Skin Grafting.

Ear skin from an allogeneic B6 donor mouse was placed on graft beds of approximately 8 mm2 on the flanks of anesthetized recipient mice. Grafts were covered with Vaseline gauze and fixed with fabric strips. Bandages were removed 7 days later, and grafts were monitored every other day for signs of rejection. Grafts were considered rejected when >80% of the graft area was necrotic.

Mice.

NU/J mice were obtained from Jackson Laboratories. Mice used in this study were maintained according to protocols approved by the UCSF Institutional Care and Use of Animals Committee (IACUC).

Statistics.

Data was analyzed with GraphPad Prism software using unpaired two-tailed Student's t test or Mann-Whitney test. Error bars in bar diagrams represent standard deviation of the samples.

Example 1: In Vitro Directed Differentiation of hESCs into TEPs

Even though the molecular mechanisms responsible for specifying thymus fate are still uncertain, prior work has identified the Foxn1 and Hoxa3 transcription factors as early and essential regulators of thymus specification and of differentiation of TEPs into mature TECs (Manley and Capecchi, 1995; Nehls et al., 1996). Therefore efforts were focused on developing a stepwise protocol that recapitulates thymus organogenesis by using Foxn1 and Hoxa3 expression as readouts for thymic specification.

As summarized in FIG. 1A, hESCs were sequentially differentiated into DE, AFE, ventral pharyngeal endoderm (VPE), and TEPs. Activin A was used to induce differentiation of hESCs into DE (D'Amour et al., 2005). At the end of stage 1, the majority of the cells co-expressed Sox17 and Foxa2, confirming efficient specification to DE (FIG. 7A). Next, to promote the development of anteriorized and ventralized endoderm competent to give rise to Foxn1+ Hoxa3+ TEPs, we added activators and inhibitors of signaling pathways that have been shown to influence anterior-posterior and ventral-dorsal identities of emerging definitive endoderm (Zorn and Wells, 2009). We found that treatment of hESCs with high levels of activin A for 5 days (stage 1), followed by the addition of BMP4, RA, and the TGFβ inhibitor LY364947 (stage 2 and 3), and then BMP4 and RA alone (stage 4), led to a significant increase in FOXN1 and HOXA3 expression over undifferentiated hESCs at the end of stage 4 (FIG. 1B, condition 6). In addition, hESCs differentiated under these conditions expressed EYA1 and GCM2, two markers found in the developing third pharyngeal pouch (FIG. 7B), thus confirming the formation of pharyngeal endoderm (PE) in our cultures. Interestingly, HOXA3 and EYA1 expression levels obtained with these culture conditions were not as high as those observed with other treatments (FIGS. 1B and 7B, conditions 1-5). These observations suggest that specification to the thymic lineage occurs more efficiently when the levels of expression of these key factors remain below a certain threshold. (FIGS. 1B and 7B, conditions 2-6).

Next, to optimize the efficiency of differentiation of AFE to VPE and to TEPs, cells were differentiated up to stage 2 with condition 6 before being exposed to additional molecules involved in pharyngeal pouch patterning or involved directly in the induction of Foxn1 expression (Balciunaite et al., 2002, Nature Immunology 3, 1102-1108; Frank et al., 2002; Bleul and Boehm, 2005, J Immunol 175, 5213-5221; Moore-Scott and Manley, 2005, Dev Biol 278, 323-335; Gordon et al., 2010, Dev Biol 339, 141-154; Neves et al., 2012, Dev Biol 361, 208-219). We found that the simultaneous addition of BMP4, RA, Wnt3a, FGF8b, and the Sonic Hedgehog (Shh) inhibitor cyclopamine at stages 3 and 4 led to an even more robust induction of Foxn1, while maintaining levels of HOXA3 and EYA1 similar to those found in human fetal thymus (FIGS. 1B and 7B, condition 7). Immunostaining and flow cytometry analysis of cultures at the end of stage 4 confirmed that a significant number of cells differentiated under these conditions co-expressed Hoxa3 (13.7±2.8%) and EpCAM (95±3%), an epithelial marker expressed by many epithelial cells, including TEPs (Rossi et al., 2006) (FIG. 1C and FIG. 7C). This method thus yielded approximately 0.14 HOXA3+EpCAM+ double positive output cells per input hESC. Additional gene expression analysis for markers of other endoderm derivatives revealed that, while markers of thyroid (NKX2.1, PAX8), lung (NKX2.1, FOXP2), parathyroid (PTH), and pancreas (PDX1) were not expressed, liver markers (AAT, ALB, CYP3A4, CYP3A7) could be detected (FIG. 7D), suggesting that some cells were specified to the liver lineage. Given that Foxn1 is also expressed in skin epithelial cells, we further tested for the presence of markers of early skin differentiation (KRT1 and KRT10). The absence of such markers (FIG. 7D) rules out the possibility that the induction in FOXN1 expression was due to the generation of ectoderm-derived skin cells in the cultures. The optimized differentiation protocol (condition 7) was also tested on HUES4 cells to assess efficiency in another hESC line. As shown in FIGS. 7E-G, FOXN1 and HOXA3 mRNA transcription, as well as Hoxa3 and EpCAM protein expression, were significantly induced. These data indicate that the differentiation protocol can be applied to other pluripotent stem cell lines. Taken together, these results demonstrate that efficient commitment of hESCs to the thymic lineage can be attained by precisely regulating the activities of TGFβ, BMP4, RA, Wnt, Shh, and FGF signaling throughout differentiation.

FIG. 1.

Directed differentiation of hESCs into TEPs. (A) Schematic of differentiation protocol and marker genes for specific stages. ES, embryonic stem cells; DE, definitive endoderm; AFE, anterior foregut endoderm, VPE, ventral pharyngeal endoderm; TEP, thymic epithelial progenitors; TEC, thymic epithelial cells. (B) Gene expression analysis of day 11 hESCs treated with the indicated factor combinations (conditions 1-7) (n=4-10). Fetal and adult human thymus samples served as controls. Values are normalized to TBP, are relative to undifferentiated hESCs, and are shown as mean±SD. Dash lines correspond to fetal expression levels that were used as a guide to optimize the differentiation protocol ($P^* < 0.05$, $^{} < 0.01$, $^{*} < 0.001$, unpaired Student's t test, compared to undifferentiated hESCs). (C) Immunofluorescence analysis of stage 4 cultures differentiated with condition 7 for HOXA3 (green) and EpCAM (red) protein expression. Nuclei were stained with DAPI. Scale bar=50 μm.

FIG. 7. Induction of DE, PE and TEP Markers in hESC Cultures. (A)

Immunofluorescence analysis of day 5 cultures differentiated with condition 7 for Foxa2 (green) and Sox17 (red) protein expression. Nuclei were stained with DAPI. Scale bar=50 μm. (B) Gene expression analysis of day 11 hESC cultures treated with the indicated factor combinations (FIG. 1B, conditions 1-7) (n=4-10). Fetal and adult human thymus samples served as controls. Dash line corresponds to fetal expression levels that were used as a guide to optimize the differentiation protocol. Values are normalized to TBP, are relative to undifferentiated hESCs, and are shown as mean±SD. (P*<0.05, <0.01, *<0.001, ****<0.0001, unpaired Student's t test, compared to undifferentiated hESCs). (C) Flow cytometry analysis of stage 4 cultures differentiated with condition 7 showing that most of the cells are positive for EpCAM. Gray line represents isotype control. (D) hESCs cultures differentiated using condition 7 also express liver markers (AAT, ALB, CYP3A4, CYP3A7) but not thyroid (NKX2.1, PAX8), lung (NKX2.1, FOXP2), parathyroid (PTH), pancreas (PDX1) or skin (KRT1, KRT10) markers. Values are normalized to TBP, are relative to undifferentiated hESCs, and are shown as mean±SD. (E) Gene expression analysis of undifferentiated HUES4 (n=9), day 11 HUES4 cultures treated with condition 1 (HUES4 control) (n=4) or 7 (HUES4 TEP) (n=6). Values are normalized to TBP, are relative to undifferentiated hESCs, and are shown as mean±SD. (P*<0.05, **<0.01, unpaired Student's t test, compared to undifferentiated hESCs). (F) Flow cytometry analysis of day 11 HUES4 (n=2) cultures treated with condition 7 showing that most of the cells are positive for EpCAM. Gray line represents isotype control. (G) Immunofluorescence analysis of day 11 HUES4 cultures differentiated with condition 7 for Hoxa3 (green) and EpCAM (red) protein expression. Nuclei were stained with DAPI. Scale bar=50 µm.

Example 2: hESC-Derived TEPs Mature into TECs In Vivo

Figure 8:
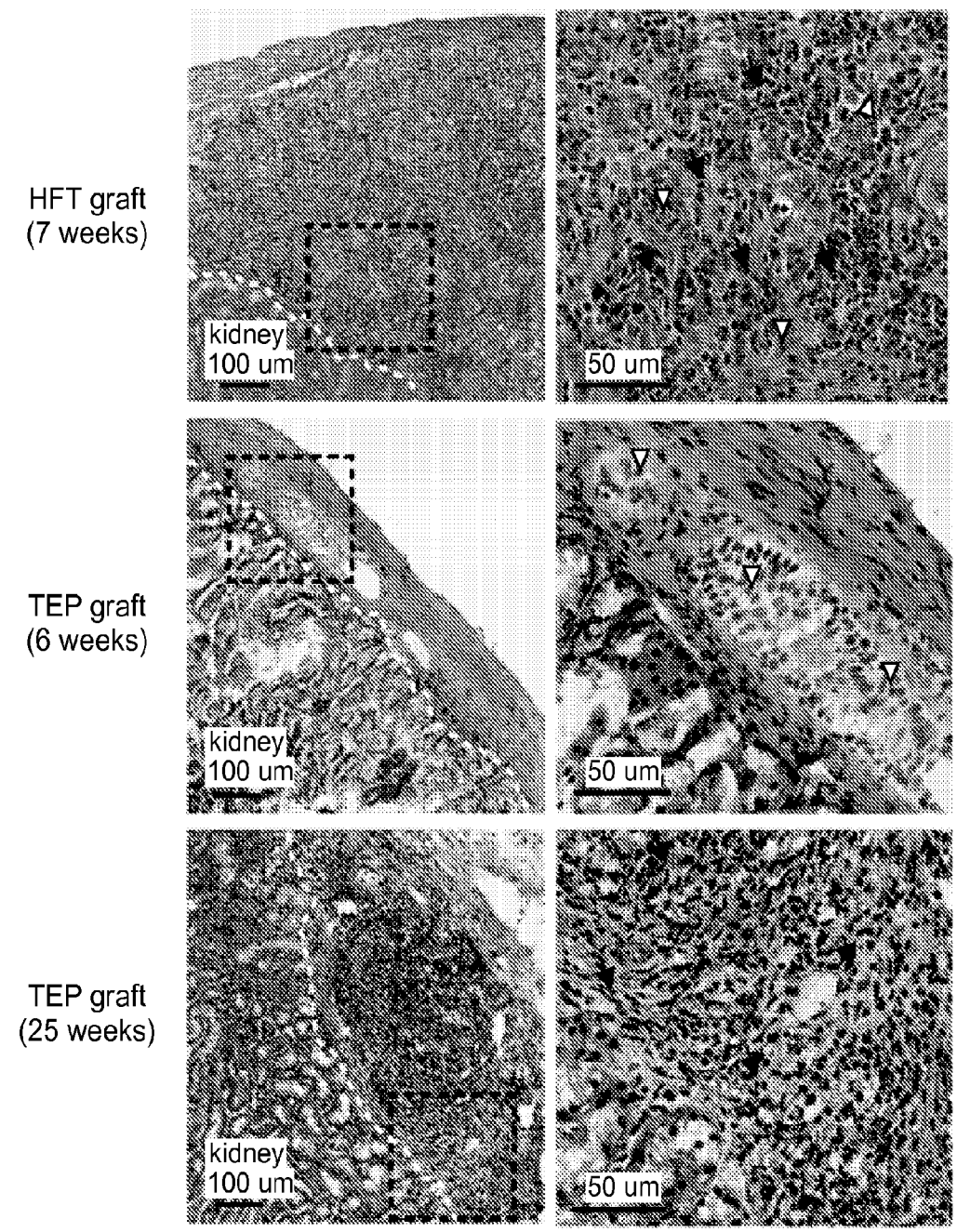
FIG. 8 shows histology of grafts recovered from nude mice.

Although differentiated cells in our cultures express genes important for thymic identity such as FOXN1, HOXA3, and EYA1, marker genes characteristic of mature TECs such as HLA-DRA (MHC class II molecule) and AIRE were not detected (data not shown). This was not surprising since interactions of TEPs with developing T cell progenitors are necessary to stimulate maturation into functional TECs (Shores et al., 1994, Int. Immunol. 6, 1393-1402; Hollander et al., 1995, Nature 373, 350-353; Klug et al., 2002, J Immunol 169, 2842-2845). To test the capacity of in vitro generated TEPs to further mature, we transferred them to an environment where they would be in contact with lymphoid progenitors. We employed nude mice carrying a mutation in Foxn1 that prevents the development of a functional thymus without precluding the formation of a lymphoid progenitor compartment. hESC-derived TEPs were thus transplanted under the kidney capsule of nude mice and grafts were analyzed 8 to 20 weeks later for the expression of genes found in mature TECs. Nude mice grafted with human fetal thymus (HFT) were used as positive controls. As shown in FIG. 2A, while FOXN1 was expressed at similar levels in grafts when compared to in vitro differentiated TEPs, a substantial upregulation in the expression of the differentiated TEC marker genes HLA-DRA, DLL4, CCL25, CXCL12 and SCF was observed in TEP grafts (FIG. 2A), indicating increased maturation of TEPs upon transplantation. Expression of AIRE was not detected in TEP grafts. Furthermore, histological analysis of hematoxylin-eosin stained grafts and immunofluorescence analysis using an antibody recognizing a wide spectrum of different cytokeratins demonstrated the presence of epithelial structures in the grafts (FIGS. 2B and 8). More importantly, antibodies for cytokeratin marking mature mTECs (K5) and cTECs (K8) revealed K5- and K8-positive areas resembling normal thymic architecture in the TEP grafts, similar to that observed in HFT grafts (FIG. 2C). These results suggest that K5+K8+ TEPs in hESC-derived grafts can give rise to K5+K8− mTECs and K5−K8+ cTECs in vivo. Taken together, these data indicate that hESC-derived TEPs acquire characteristics of mature TECs upon transplantation into athymic nude mice.

FIG. 2.

hESC-derived TEPs mature into TECs in vivo. (A) Gene expression analysis of undifferentiated hESCs (n=4), hESCs differentiated with condition 7 (n=4) and grafts recovered from HFT (n=5) and TEPs (n=6) recipient nude mice (8-20 weeks after transplantation). Fetal and adult human thymus samples served as controls. Values represent mean±SD (P*<0.05, Mann-Whitney test, compared to TEPs d11). (B, C) Immunofluorescence analysis of HFT and TEP grafts recovered from nude mice (8 weeks after transplantation). (B) Epithelial cells within grafts were identified using a wide spectrum cytokeratin antibody (red). hESC-derived tissue is demarcated from the kidney by white dashed lines. Scale bar=100 µm. (C) Cytokeratin 8 (K8) (green) and cytokeratin 5 (K5) (red) staining identify cortical and medullary TECs, respectively, while K5$^+$/K8$^+$ double positivity (yellow) indicates progenitor cells. Insets display higher magnification of dashed line areas, showing the three cell types in close proximity. Scale bar=50 µm.

FIG. 8. Histology of Grafts Recovered from Nude Mice.

Hematoxylin and eosin staining of grafts harvested 7 weeks (HFT) or 6 and 25 weeks (TEP) after transplantation demonstrated the presence of epithelial cells (blue arrowheads) and immune cells (black arrows) in the grafts. hESC-derived tissue is demarcated from the kidney by white dashed lines. A higher magnification of areas outlined by dashed black lines is shown.

Example 3: hESC-Derived TECs Support the Development of New T Cells

In addition to providing an appropriate environment for the maturation of TEPs into TECs, this experimental system also allows for testing of the functionality of transplanted cells. Indeed, when provided with functional thymic tissue from mouse (Gordon et al., 2004, Nature Immunology 5, 546-553; Bleul et al., 2006, Nature 441, 992-996) or human origin (Kollmann et al., 1993, J Exp Med 177, 821-832), the lymphoid progenitors of nude mice can develop into mature T cells through the typical stepwise progression of CD4$^-$CD8$^-$ double negative (DN), CD4$^+$CD8$^+$ double positive (DP), and mature single positive (SP) CD4$^+$ or CD8$^+$ T cells. To assess the functionality of transplanted TEPs generated using our method, we monitored the emergence of DP and SP T cells in the peripheral blood, secondary lymphoid organs, and grafts. Mice grafted with either hESCs differentiated with a control protocol (spontaneous hESCs differentiation in the absence of signaling factors) or HFT, served as negative and positive controls, respectively.

Figure 3:
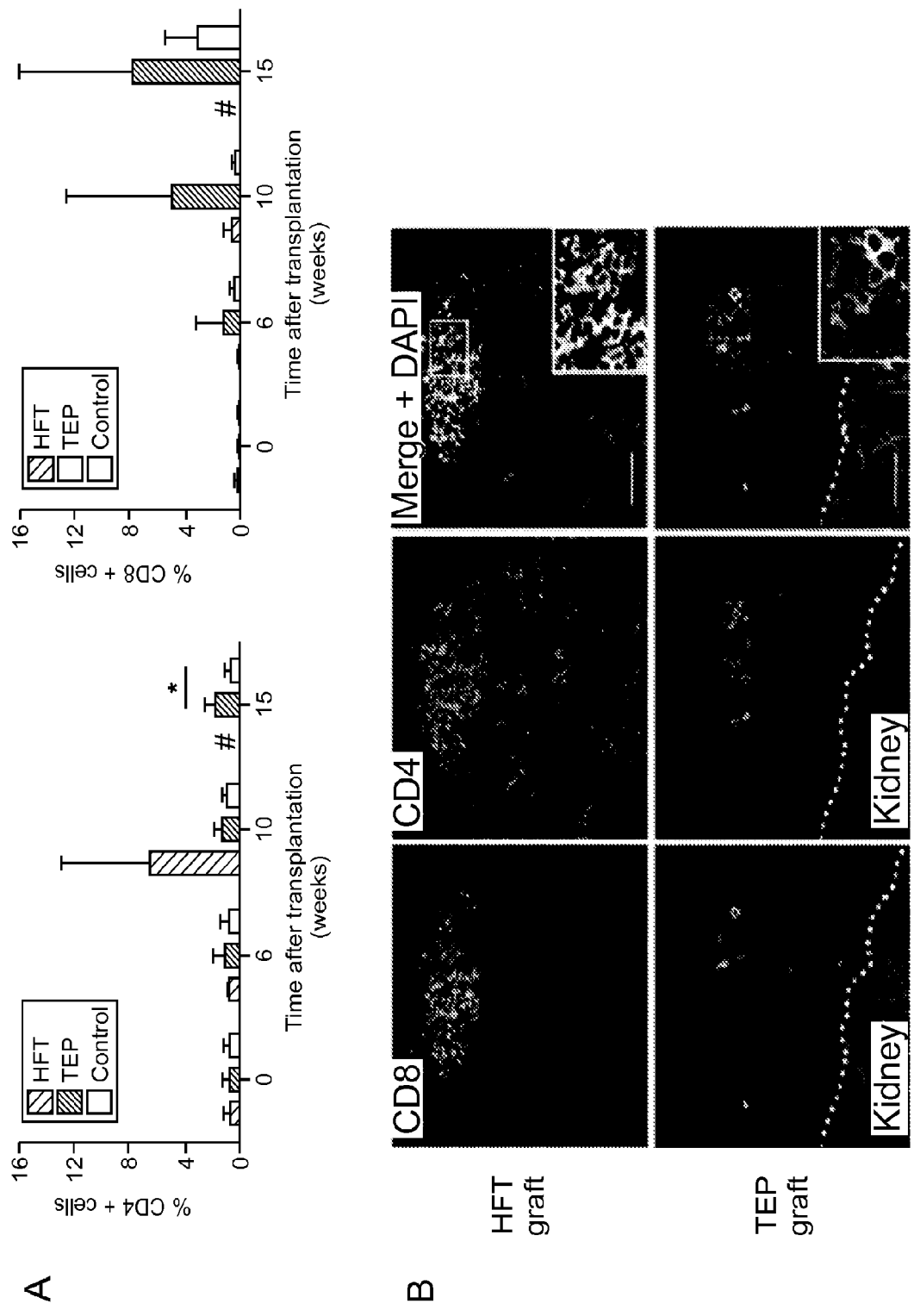
FIG. 3 (A-E) illustrates that hESC derived TEP cells support development of T cells in athymic mice.
Figure 3:
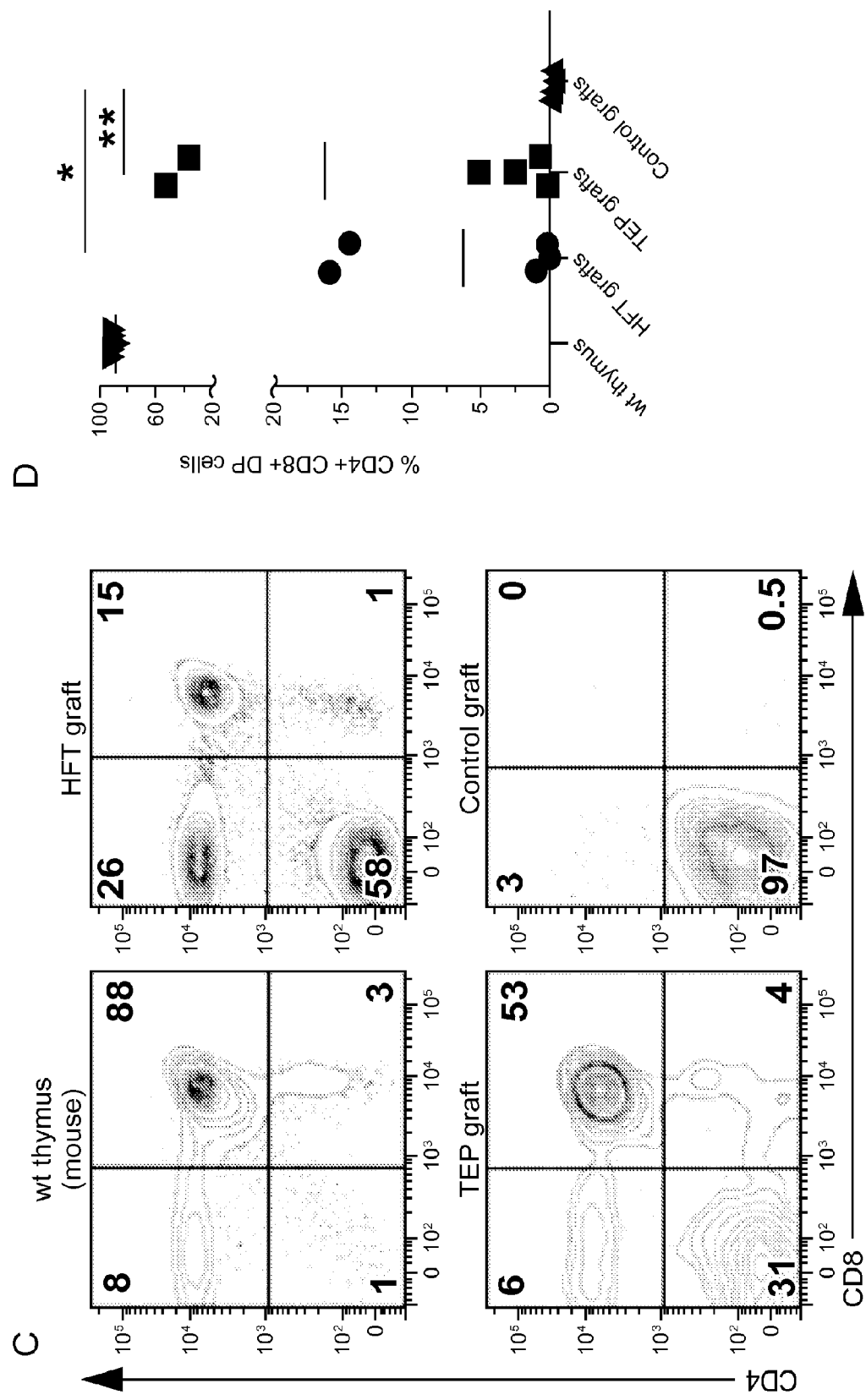

As reported previously, a small number of extrathymically generated CD4$^+$ and CD8$^+$ SP T cells were detected in the peripheral blood and spleens of non-grafted and control-grafted nude mice (FIGS. 3A and 4A) (Kennedy et al., 1992, J Immunol 148, 1620-1629; Bleul et al., 2006, supra).

Figure 9A:
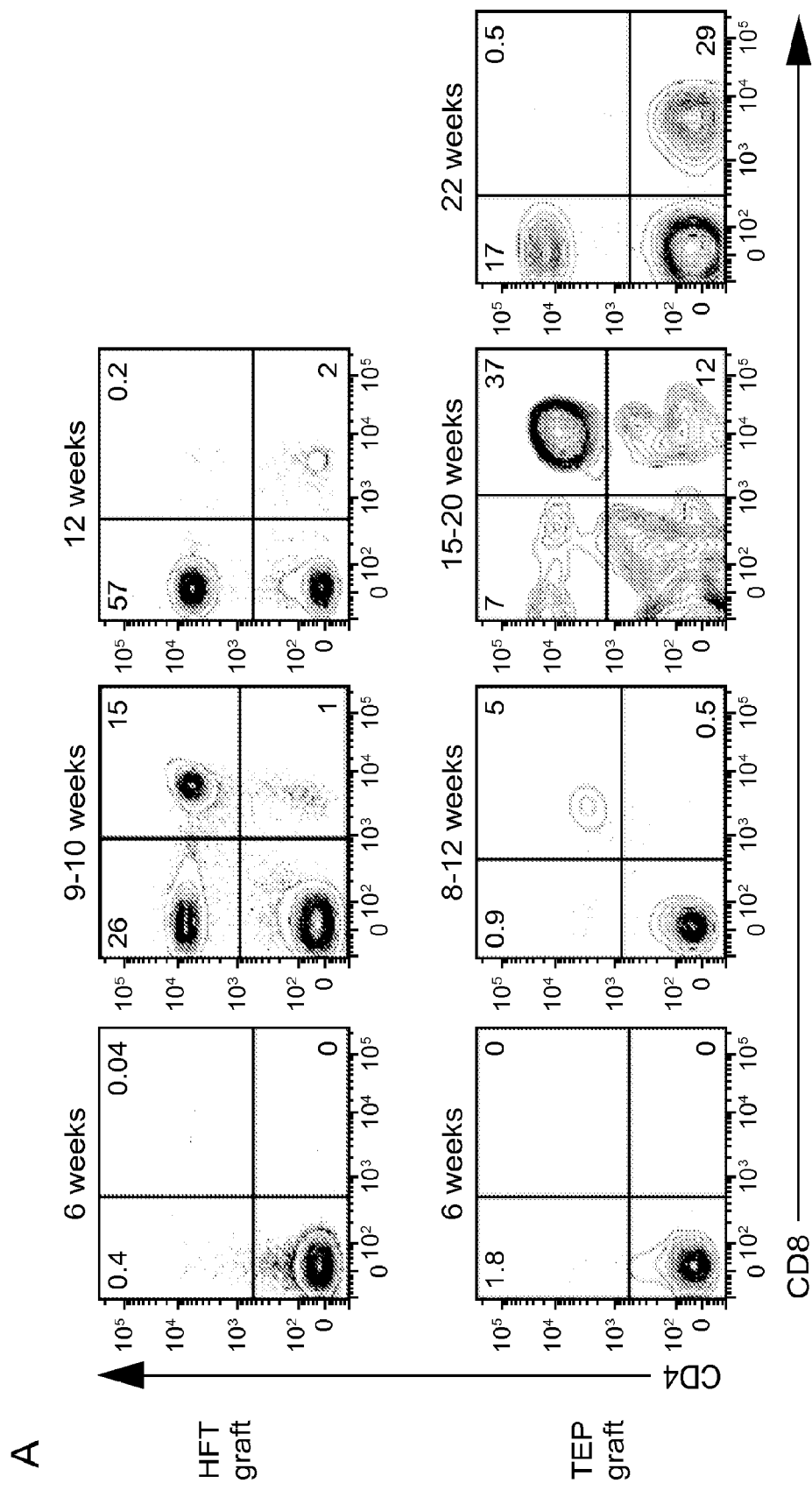
FIG. 9 (A-D) depicts kinetics and extent of thymopoiesis in HFT and TEP recipient nude mice.

However, starting approximately 10 weeks post transplantation, we observed an increase in the number of CD4+ and CD8+SP T cells specifically in the peripheral blood of TEPs and HFT recipient mice (FIG. 3A), suggesting that transplanted TEPs could support the generation of new T cells. Consistent with this result, immunofluorescence and flow cytometry analysis of grafts harvested 4 to 12 weeks (for HFT) or 8 to 25 weeks (for TEPs and controls) after transplantation revealed that CD4$^+$CD8$^+$ DP as well as CD4$^+$ and CD8+ SP T cells could be detected in TEP and HFT grafts, but not in control grafts (FIGS. 3B-3D and 9A-9D). These results confirmed that hESC-derived TEPs could indeed support thymopoiesis upon transplantation into athymic mice. Notably, similar to what is observed during the progression from DP to SP T cells in a normal mouse thymus, the T-cell receptor (TCR) complex proteins CD3 and TCRβ were properly expressed on DP and SP T cells from TEP and HFT grafts (FIG. 3E), indicating successful T cell receptor gene rearrangement and positive selection of newly generated T cells. Immunofluorescence analysis of HFT and TEP grafts for the mitotic marker Ki67 showed low levels of proliferating cytokeratin+ cells in HFT and TEP grafts (FIG. 9C) whereas most CD3+ T cells were found negative for Ki67 (FIG. 9D). While we saw clear evidence for canonical T cell maturation, we also observed variations in the kinetics and extent of thymopoiesis between TEP-grafted and HFT-grafted mice as well as between mice of the same group (FIGS. 3A-3D and 9A-9D). A likely explanation comes from the differences in the developmental stage of TECs in HFT grafts when compared to hESC-derived TEPs, as well as from variations in engraftment efficiency. Thymopoiesis was also not sustained over prolonged periods of time as revealed by the progressive decline in the number of DP T cells in both TEP grafts and HFT grafts (FIG. 9A-9B). Since nude mice possess residual NK cell activity and can also develop autoimmunity in multiple organs following xenogeneic transplantation of thymic tissue (Taguchi et al., 1986, J Exp Med 164, 60-71; Fudaba et al., 2008, The Journal of Immunology 181, 7649-7659), it is possible that the grafts are being damaged over time, leading to a decrease in thymopoiesis. Taken together, the increase in CD4+ and CD8+ SP T cells in the peripheral blood of TEP-grafted mice combined with the presence of CD4+CD8+ DP and SP T cells in the grafts clearly demonstrate that hESC-derived TEPs can support the development of new T cells.

FIG. 3.

hESC-derived TECs support T cell development in athymic mice. (A) Flowcytometric analysis of cells isolated from peripheral blood of HFT (n=2-6), TEPs (n=4-10), and control (n=3-10) nude recipients for the presence of mouse CD4+ and CD8+ SP Tcells. (P*<0.05, unpaired Student's t test, compared to control); #, similar to what has been reported with other xenografts in nude animals (Taguchi et al., 1986, supra; Fudaba et al., 2008, supra), mice grafted with HFT started showing signs of autoimmunity and were sacrificed before 15 weeks. (B) Immunofluorescence analysis of HFT and TEP grafts recovered from nude mice for the presence of mouse CD8+(green), CD4+(red) and CD8+CD4+DP (yellow) T cells. hESC-derived tissue is demarcated from the kidney by white dashed lines. Scale bar=50 μm. (C, D and E) Flow cytometric analysis of cells recovered from wt mouse thymus, HFT, TEP, and control grafts for the presence of mouse CD4+ (red), CD8+ (blue) and CD4+CD8+ DP (green) T cells. (C) Representative plots from wt mouse thymus and grafts harvested 9 weeks (HFT) or 15 weeks (TEPs and control) after transplantation. (D) Quantification of the percentage of mouse DP T cells in wt mouse thymus (n=5), HFT (n=5), TEP (n=6), and control (n=6) grafts harvested 4-12 weeks (HFT) or 8-22 weeks (TEP and control) after transplantation (P*<0.05, **<0.01, Mann-Whitney test). (E) Cell surface expression of T cell markers CD3 and TCRβ on DP T cells (green), CD4+ SP T cells (red) and CD8+ SP T cells (blue).

Figure 9:
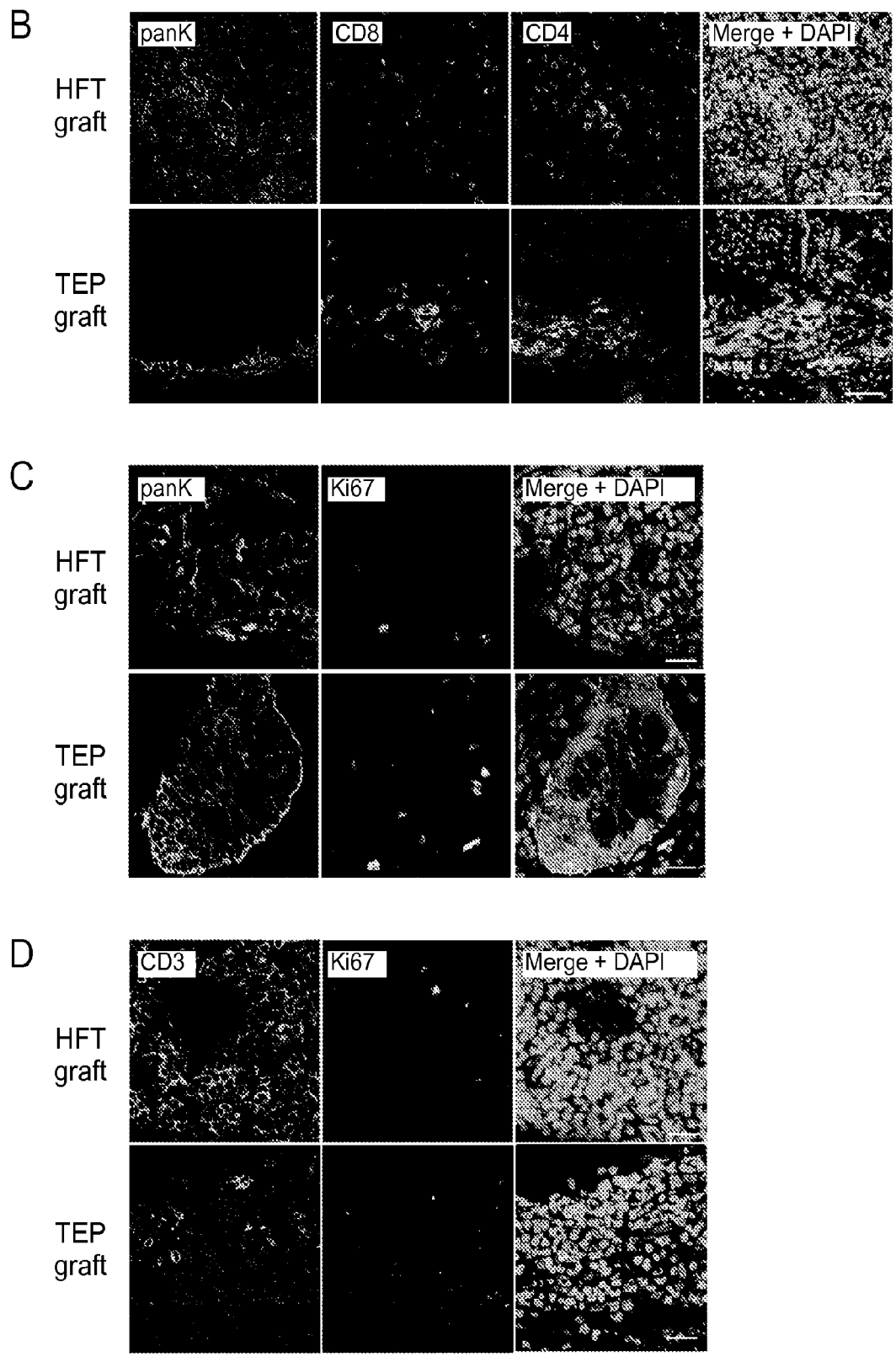

FIG. 9. Kinetics and Extent of Thymopoiesis in HFT and TEP Recipient Nude Mice.

(A) Flow cytometric analysis of cells recovered from grafts for the presence of mouse CD4 and CD8 SP and DP T cells. Grafts were harvested 6 to 12 weeks (HFT) or 6 to 22 weeks (TEPs) after transplantation. Data shown are after gating for lymphocytes with light-scatter parameters and exclusion of dead cells by staining with DAPI. n=1-3 for each time point. (B) Immunofluorescence analysis of HFT and TEP grafts recovered from nude mice for the presence of cytokeratin+ cells (white), mouse CD8+ T cells (green), and mouse CD4+ T cells (red). Grafts were harvested 14 weeks (HFT) or 15 weeks (TEP) after transplantation. Scale bar=50 μm. (C) Proliferation of cytokeratin+ cells (green) in HFT and TEP grafts was determined by co-staining with the mitotic marker Ki67 (red). Scale bar=25 μm. (D) Proliferation of mouse CD3+ cells (green) in HFT and TEP grafts was determined by co-staining with Ki67 (red). Scale bar=25 μm.

Example 4: T Cells Generated in TEP-Recipient Nude Mice are Functional

In addition to the T cells detected in the grafts, we also found evidence of migration of functional T cells to the peripheral immune system in TEP-grafted mice. As shown in FIGS. 4A and 4B, a significant increase in CD4+ and CD8+ SP T cell populations, and more prominently, in TCRβ+CD4+ and TCRβ+CD8+ T cells, could be detected in the spleen of HFT and TEP-grafted mice over non-grafted and control-grafted mice. Importantly, we also observed positive selection of CD4+Foxp3+ regulatory T cells (Tregs), a subset of lymphocytes essential for establishing immune tolerance through suppression of autoreactive T cells (Sakaguchi, 2000, Cell 101, 455-458). In HFT and TEP-grafted mice, 4.6±1.8% and 2.9±0.8% of total CD4+ cells were positive for Foxp3, whereas only 0.5±0.4% and 0.2±0.1% were positive in control and non-grafted mice, respectively (FIG. 4C). Thus, not only did we observe increased formation of T cells, hESC-derived TEPs also promoted formation of T cell subsets otherwise almost completely absent in control animals.

Figure 10:
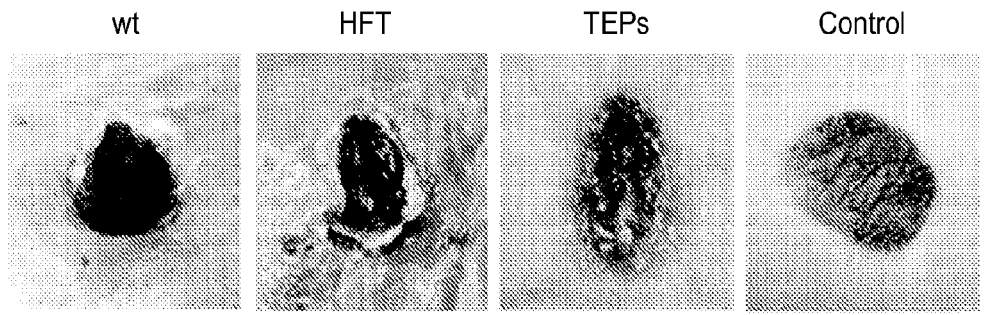
FIG. 10 shows transplantation of allogeneic skin grafts.

Furthermore, spectratype analysis of the TCR repertoire of cells recovered from nude recipient mice indicated more diverse TCR Vβ rearrangements in HFT and TEP-recipients in comparison to control mice (FIGS. 4D and 4E), demonstrating that hESC-derived TECs can support the development of T cells with a diverse TCR repertoire. Another critical test for T cell function is their ability to proliferate upon TCR stimulation. Labeling of cells with carboxyfluorescein diacetate succinimidyl ester (CFSE) followed by stimulation with anti-CD3/CD28 antibodies revealed that 74±6% of CD4+ and 84±6% of CD8+ T cells isolated from HFT-grafted mice and 47±3% of CD4+ and 68±5% of CD8+ T cells isolated from TEP-grafted mice proliferated following TCR stimulation (FIG. 4F). These results indicate that a significant portion of newly formed T cells is functional and responsive to activation signals through the TCR. Relative to wild-type (wt) mice, lower TCR diversity and lower levels of TCR stimulation-induced proliferation were seen in HFT and TEP-grafted mice (FIGS. 4E and 4F), consistent with cross-species differences that likely impair full activation/differentiation of murine T cells upon interaction with human TECs (Taguchi et al., 1986, supra; Kollmann et al., 1993, supra; Fudaba et al., 2008, supra). In addition, significant proliferation of T cells from HFT-grafted mice and CD8+ T cells from TEP-grafted mice was observed in response to allogeneic stimulator cells (FIG. 4G), indicating that T cells are capable of allogeneic responses. CD4+ T cells from HFT-grafted mice and CD8+ T cells from TEP-grafted mice also proliferated in response to stimulator cells from nu/+ mice (FIG. 4H). This result supports the idea that T cells in HFT and TEP-grafted mice have been selected on human MHC and are thus responding to MHC-mismatched stimulator cells. As an additional measure of functionality, we evaluated the ability of grafted mice to reject allogeneic skin transplants. As shown in FIGS. 4I and 10, we observed increased graft rejection in HFT (median survival time or MST=20.5 days) and TEP (MST=21 days) recipient nude mice when compared with control mice (MST>35 days), confirming that the T cells generated in HFT and TEP-grafted mice are functional. Summarily, these data confirm the ability of transplanted TEPs to support the generation of new functional T cells in athymic nude mice.

Figure 4:
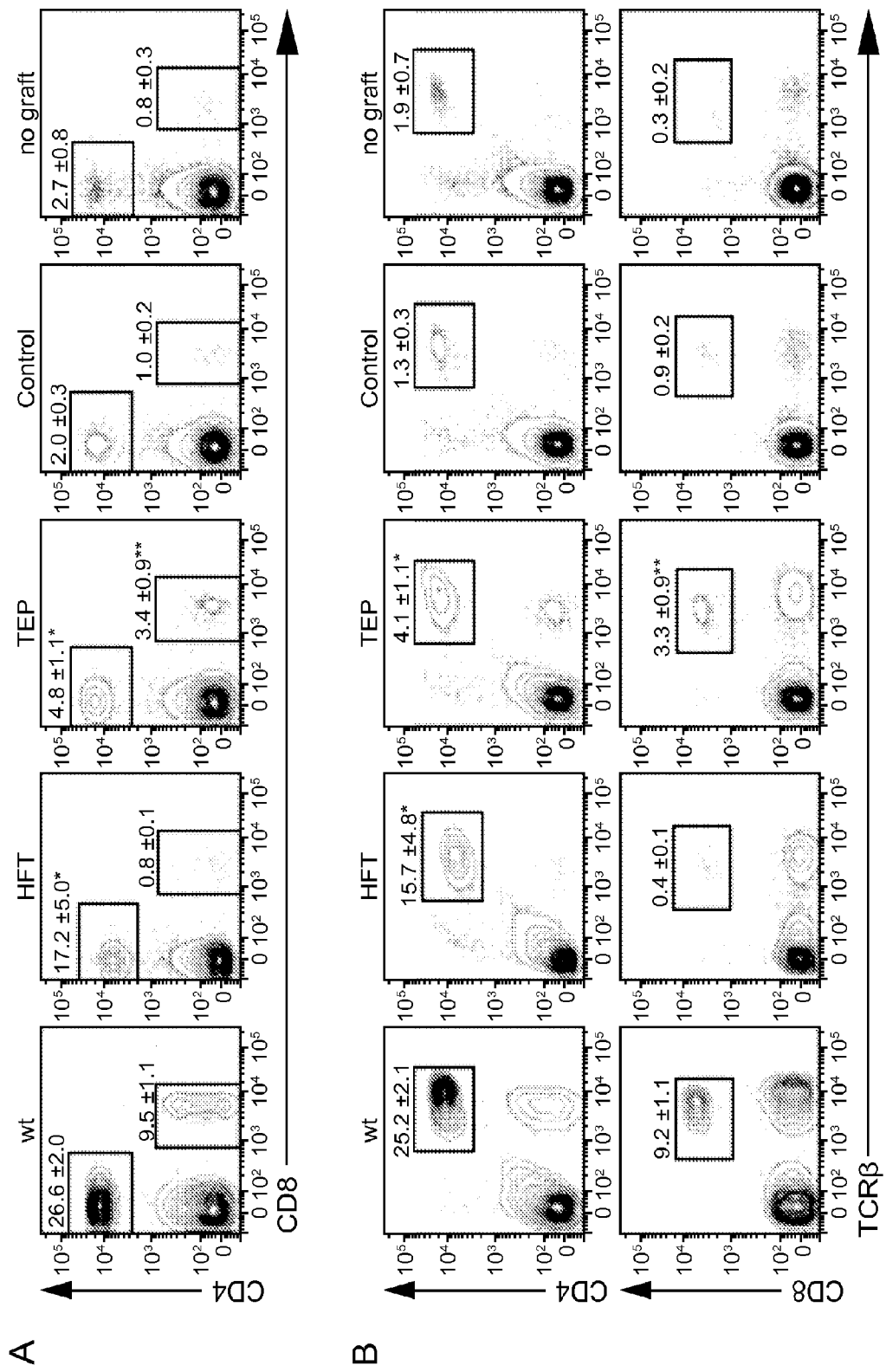
FIG. 4 (A-I) illustrates generation of functional T cells in nude mice implanted with hESC derived TEP cells.
Figure 4:
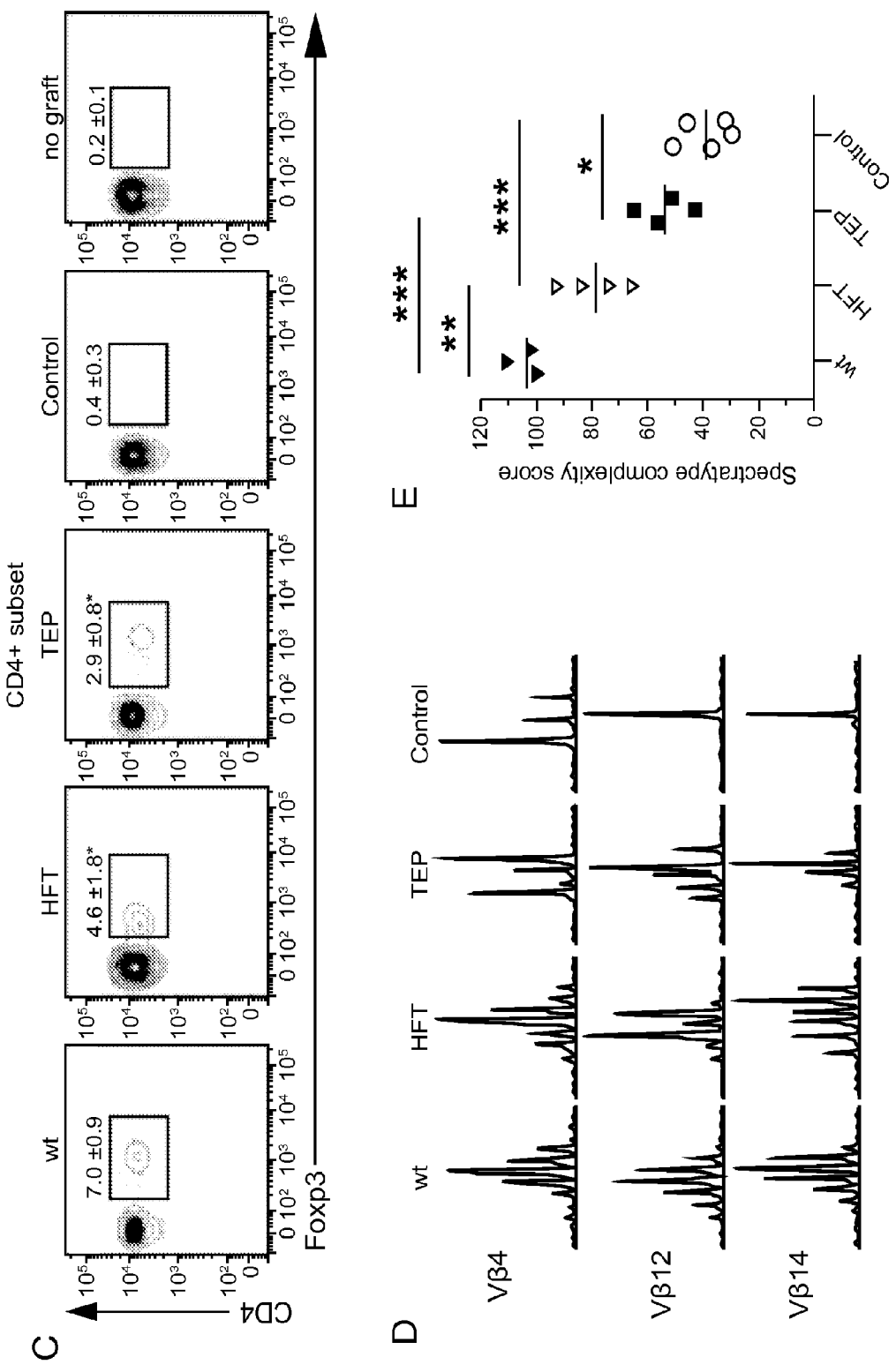
Figure 4:
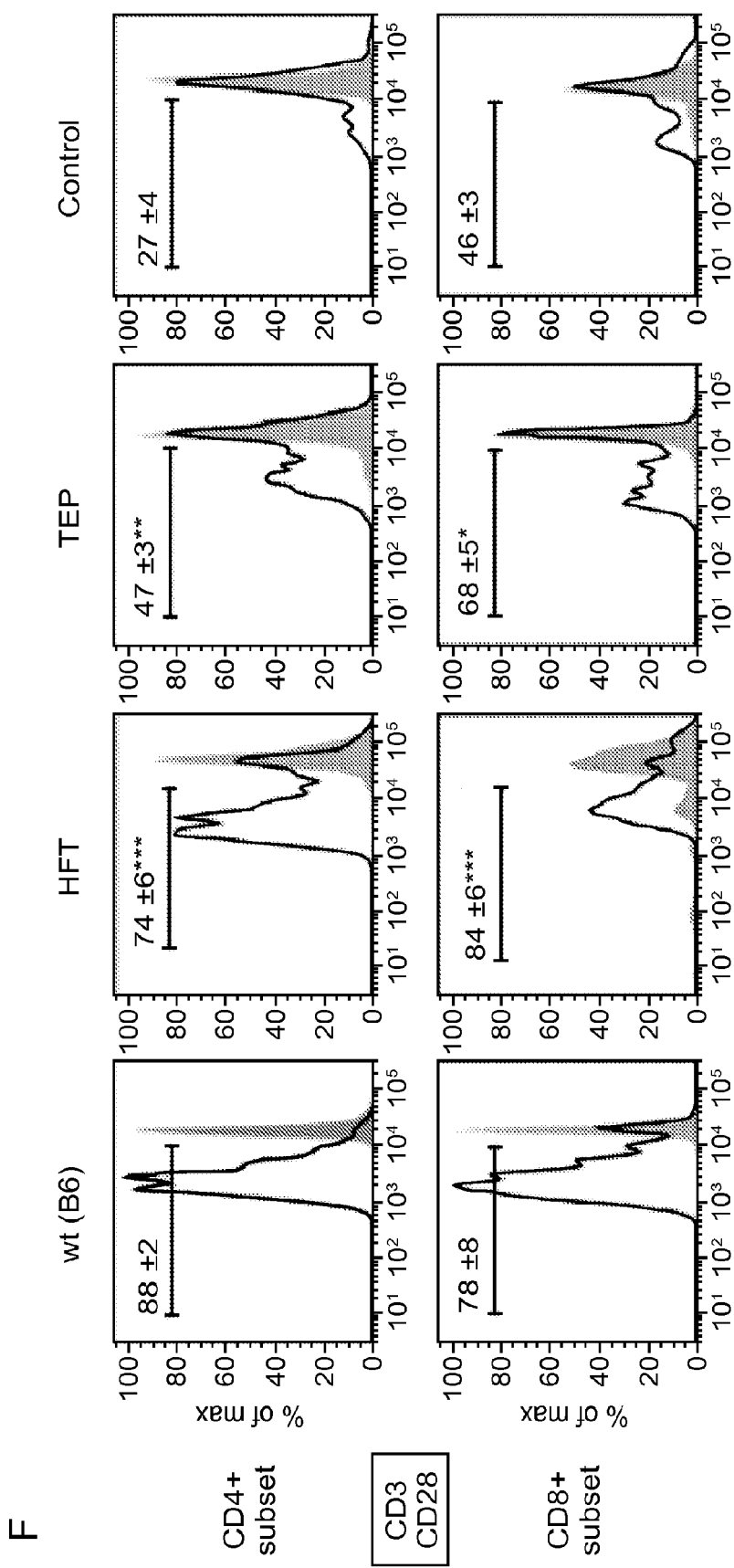
Figure 4:
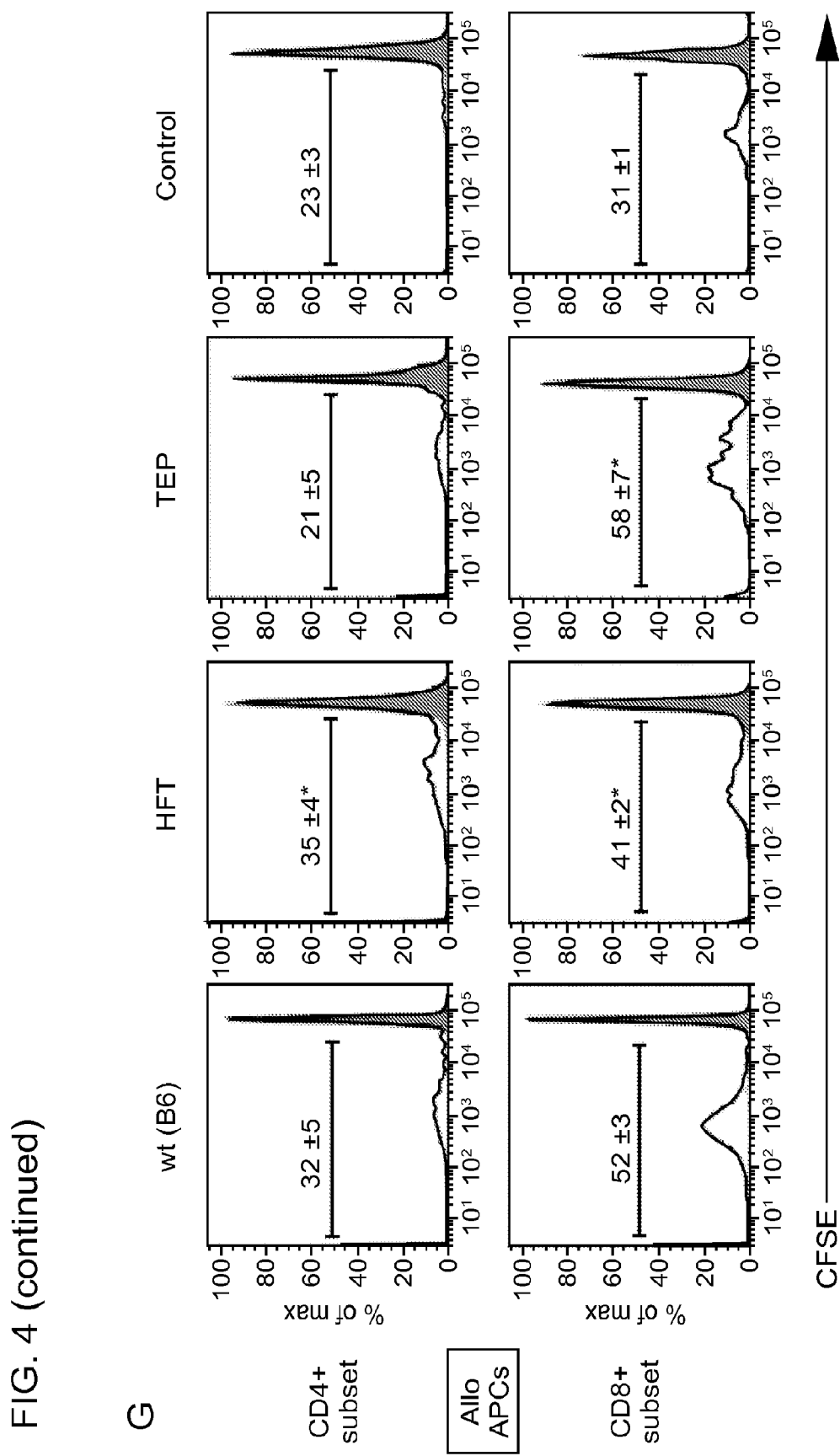
Figure 4:
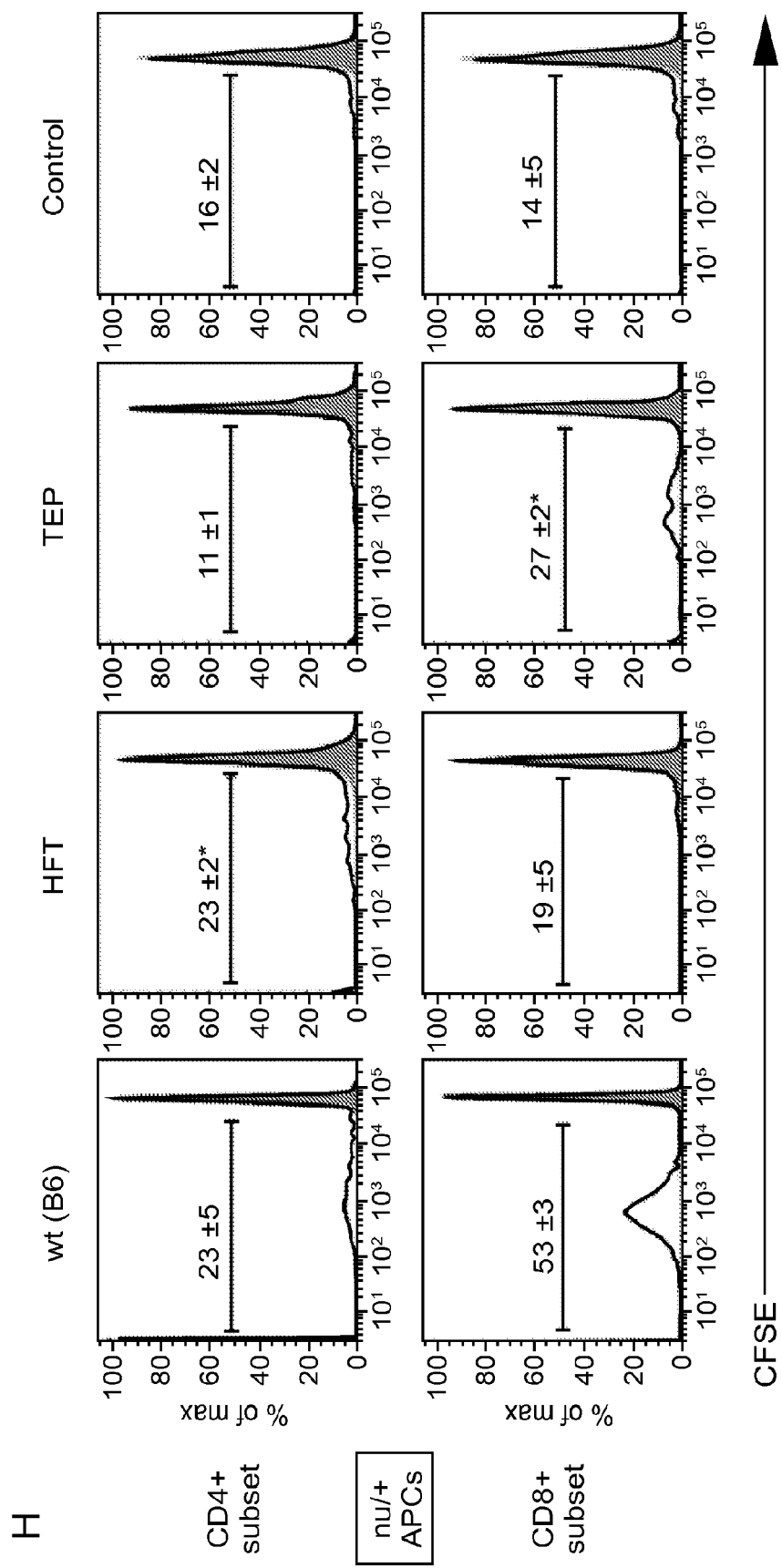
Figure 4:
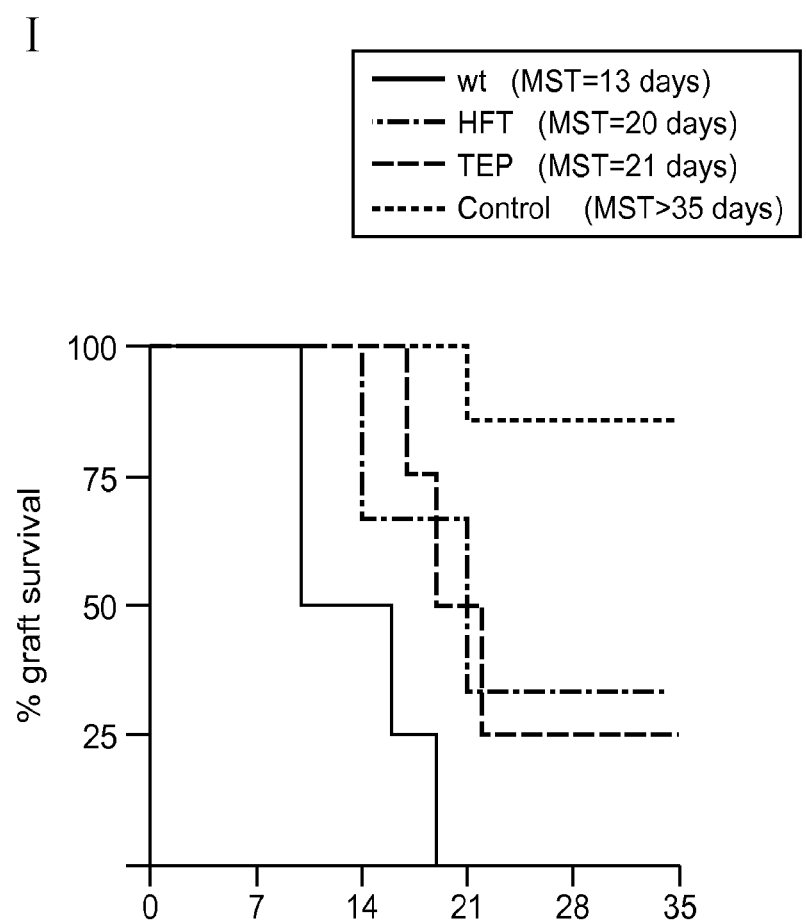

FIG. 4. New functional T cells are generated in TEP-recipient nude mice. (A, B and C) Splenocytes recovered from wt (n=4), HFT (n=8), TEP-grafted (n=4), control-grafted (n=5), and non-grafted (n=5) nude mice were analyzed by flow cytometry for mouse CD4, CD8, TCRβ and Foxp3 expression. (A) Percentage of CD4$^+$ (red) and CD8$^+$ (blue) splenocytes. (B) Percentage of CD4$^+$TCRβ$^+$ (red) and CD8$^+$TCRβ$^+$ (blue) splenocytes. (C) Percentage of Foxp3$^+$ regulatory T cells (purple) among CD4$^+$ SP T cells. (D and E) Assessment of TCR repertoire diversity by spectratype analysis of the CDR3 Vβ regions of mouse T cells recovered from spleens of wt (n=3), HFT (n=4), TEP (n=4) and control (n=5) recipient nude mice. (D) Representative spectratypes from three Vβ families are shown. (E) Spectratype complexity score representing the sum of peaks from each of the 24 Vβ family tested. (F) Proliferation of splenic T cells following in vitro TCR stimulation. Splenocytes from wt (n=4), TEP (n=4) and control (n=6) recipient nude mice were labelled with CFSE and cultured for 3 days in the presence of anti-CD3/CD28. Cells were stained for CD4 and CD8 and gated populations were analyzed by flow cytometry for CFSE levels. Non-stimulated cells are represented by shaded histograms. (P*<0.05, <0.01, *<0.001, unpaired Student's t test, compared to control). (G, H) Proliferation of enriched T cells in response to CD11c+ APCs. Enriched T cells from wt C57BL/6 (n=6-8), HFT (n=8-10), TEP (n=8-12), and control (n=4-8) recipient nude mice were labelled with CFSE and cultured for 4 days in the presence of CD11c+ APCs isolated from NOD (G) or nu/+ mice (H). Cells were stained for CD90.2, CD4 and CD8 and gated populations were analyzed by flow cytometry for CFSE levels. Non-stimulated cells are represented by shaded histograms. (P*<0.05, unpaired Student's t test, compared to control). (I) Survival of allogeneic skin grafts (from C57BL/6 mice) in nu/+(n=4), HFT (n=4), TEP (n=3), and control (n=6) recipient nude mice.

FIG. 10. Transplantation of Allogeneic Skin Grafts. Representative image of allogeneic skin grafts in nu/+, HFT, TEP, and control recipient nude mice at the time of rejection.

Example 5: Analysis of Cells Obtained from Grafts of hESC-Derived TEP Cells in a Humanized Mouse Model We tested the ability of the hESC-derived TEPs to support the maturation of human T cells in immunodeficient NOD-scid mice bearing a mutated IL-2 receptor gamma chain (NODscid-IL2Rγ or NSG mice).

Following engraftment of human hematopoietic stem cells (HSCs), NSG mice allow the development of human immune systems, including functional T and B cells capable of antiviral responses, allograft rejection, and antibody production. These humanized mice therefore represent a good model to study the hESC-derived TEPs and their ability to support the maturation of human T cells and control immune tolerance.

Figure 11:
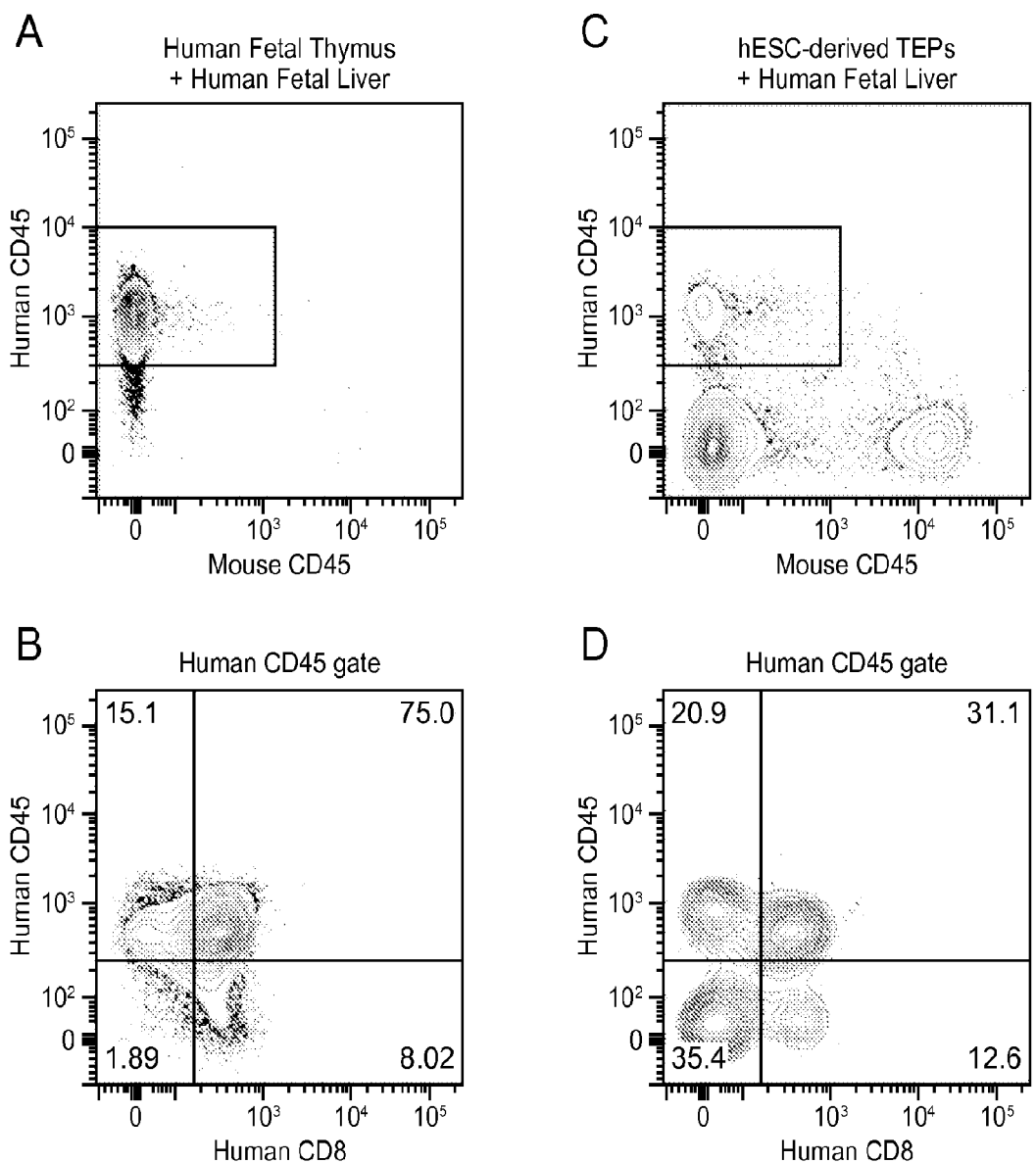
FIG. 11 (A-D) shows analysis of cells obtained from human fetal thymus/human fetal liver grafts (A-B) and hESC derived TEP cells/human fetal liver grafts in NSG mice (C-D).

To assay the functionality of the hESC derived TEPs in this humanized mouse model, we transplanted approximately $2-4 \times 10^6$ cells under the kidney capsule of NSG mice, together with a piece of human fetal liver as a source of HSCs. Mice grafted with HFT and human fetal liver under the kidney capsule served as positive controls. Flow cytometric analysis of grafts harvested 11 to 17 weeks after transplantation revealed that human CD4$^+$CD8$^+$ DP as well as CD4$^+$ and CD8$^+$ SP T cells could be detected in TEP and HFT grafts (FIG. 11). Human DP T cells were detected in 2 mice out of 6. This data demonstrates that the hESC-derived TEPs can support maturation of human T cells.

FIG. 11 depicts flow cytometric analysis of cells recovered from human fetal thymus+human fetal liver (A-B) and hESC-derived TEP cells+human fetal liver grafts (C-D) for the presence of human CD45+(A, C)), human CD8+ and human CD4+ T cells (B, D).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for generating thymic epithelial progenitor (TEP) cells, the method comprising:
    culturing definitive endodermal (DE) cells, obtained from pluripotent stem cells, in a medium comprising an activator of retinoic acid receptor, an activator of bone morphogenetic protein (BMP) signaling, and an inhibitor of transforming growth factor-β (TGF-β) signaling to produce anterior foregut endodermal (AFE) cells;
    culturing the AFE cells in a medium comprising an activator of retinoic acid receptor, an activator of bone morphogenetic protein (BMP) signaling, and an inhibitor of transforming growth factor-β (TGF-β) signaling to produce ventral pharyngeal endodermal (VPE) cells; and
    culturing the VPE cells in a medium comprising an activator of retinoic acid receptor and an activator of bone morphogenetic protein (BMP) signaling to produce the TEP cells.

2. The method of claim 1, wherein the DE cells are obtained from pluripotent stem cells by culturing pluripotent stem cells in a medium comprising a growth factor selected from the group consisting of Nodal, Activin A, and Activin B.

3. The method of claim 2, wherein the medium for culturing the AFE cells further comprises a Wnt family member, a fibroblast growth factor (FGF), and an inhibitor of hedgehog signaling.

4. The method of claim 3, wherein the medium for culturing the VPE cells further comprises a Wnt family member, a fibroblast growth factor, and an inhibitor of hedgehog signaling.

5. The method of claim 3, wherein the TEP cells express FOXN1.

6. The method of claim 2, wherein the medium for culturing the VPE cells further comprises a Wnt family member, a fibroblast growth factor, and an inhibitor of hedgehog signaling.

7. The method of claim 6, wherein the TEP cells express FOXN1.

8. The method of claim 2, wherein the TEP cells express FOXN1.

9. The method of claim 1, wherein the pluripotent stem cells are selected from the group consisting of embryonic stem cell, embryonic germ cells, and induced pluripotent stem cell.

10. The method of claim 9, wherein the pluripotent stem cells are primate pluripotent stem cells (pPS) cells.

11. The method of claim 10, wherein the pPS cells are human pluripotent stem (hPS) cells.

12. The method of claim 11, wherein the hPS cells are human embryonic stem (hES) cells.

13. The method of claim 11, wherein the hPS cells are induced pluripotent stem (iPS) cells.

14. The method of claim 1, wherein the medium for culturing the AFE cells further comprises a Wnt family member, a fibroblast growth factor (FGF), and an inhibitor of hedgehog signaling.

15. The method of claim 14, wherein the medium for culturing the VPE cells further comprises a Wnt family member, a fibroblast growth factor, and an inhibitor of hedgehog signaling.

16. The method of claim 14, wherein the TEP cells express FOXN1.

17. The method of claim 1, wherein the medium for culturing the VPE cells further comprises a Wnt family member, a fibroblast growth factor, and an inhibitor of hedgehog signaling.

18. The method of claim 17, wherein the TEP cells express FOXN1.

19. The method of claim 1, wherein the TEP cells express FOXN1.

* * * * *